United States Patent
Taniguchi et al.

(10) Patent No.: US 7,295,318 B2
(45) Date of Patent: Nov. 13, 2007

(54) APPARATUS AND METHOD FOR EVALUATING THE INTERIOR QUALITY OF FRUITS AND VEGETABLES

(75) Inventors: Norio Taniguchi, Ageo (JP); Takeshi Ohta, Komaki (JP); Motoshi Tanaka, Komaki (JP)

(73) Assignee: Mitsui Mining & Smelting Co., Ltd., Tokyo (JP)

(*) Notice: Subject to any disclaimer, the term of this patent is extended or adjusted under 35 U.S.C. 154(b) by 0 days.

(21) Appl. No.: 11/429,794

(22) Filed: May 8, 2006

(65) Prior Publication Data

US 2006/0203247 A1 Sep. 14, 2006

Related U.S. Application Data

(63) Continuation of application No. 10/191,978, filed on Jul. 9, 2002, now Pat. No. 7,151,606.

(30) Foreign Application Priority Data

Jul. 9, 2001 (JP) ............................. 2001-208020
Jun. 19, 2002 (JP) ............................. 2002-178826

(51) Int. Cl.
*G01N 21/00* (2006.01)
*G02F 1/01* (2006.01)

(52) U.S. Cl. ............... 356/432; 356/433; 250/339.11; 250/330

(58) Field of Classification Search .. 356/237.1–237.3, 356/601, 432–436, 72–73, 326, 52–68; 250/339.11, 250/339.12, 223 R, 226, 330, 910; 209/588, 209/577; 382/110

See application file for complete search history.

(56) References Cited

U.S. PATENT DOCUMENTS

| 3,938,869 A | * | 2/1976 | Josey .......................... 312/100 |
| 3,938,896 A | | 2/1976 | Selgin |
| 3,997,270 A | * | 12/1976 | Suzuki ........................ 356/634 |
| 4,281,933 A | * | 8/1981 | Houston et al. ............. 356/425 |

(Continued)

FOREIGN PATENT DOCUMENTS

JP       02-243560 A       9/1990

(Continued)

*Primary Examiner*—Sang H. Nguyen
(74) *Attorney, Agent, or Firm*—The Webb Law Firm, P.C.

(57) ABSTRACT

One form of evaluation apparatus comprising a plurality of light sources vertically arranged by one side of a carrier line in width direction Y perpendicular to carrying direction X of the carrier line; and a light-receiving section arranged by an opposite side of the carrier line in the width direction Y perpendicular to the carrying direction X of the carrier line. Another form of evaluation apparatus comprising a plurality of light sources capable of irradiating measuring lights of given quantity; means for regulating the quantity of measuring lights from the light sources in accordance with sizes of vegetables and fruits; a light-receiving window of given openness provided in a carrier line, the light-receiving window capable of leading measuring lights having been transmitted through the vegetables and fruits toward a light-receiving section; and means for regulating quantities of transmitted light provided to the light-receiving window, the means for regulating quantities of transmitted light being capable of regulating the openness of the light-receiving window.

22 Claims, 25 Drawing Sheets

U.S. PATENT DOCUMENTS

| | | |
|---|---|---|
| 4,281,993 A | 8/1981 | Shaw |
| 5,077,477 A * | 12/1991 | Stroman et al. ............ 250/349 |
| 5,237,407 A | 8/1993 | Crezee et al. |
| 5,708,271 A | 1/1998 | Ito et al. |
| 5,726,750 A | 3/1998 | Ito et al. |
| 5,845,002 A | 12/1998 | Heck et al. |
| 6,137,581 A * | 10/2000 | Kimura et al. .............. 356/433 |
| 6,271,520 B1 * | 8/2001 | Tao et al. .................. 250/330 |
| 6,512,577 B1 | 1/2003 | Ozanich |
| 6,657,722 B1 * | 12/2003 | Nagayoshi .................. 356/326 |
| 7,068,368 B1 * | 6/2006 | Nagayoshi et al. ......... 356/326 |

FOREIGN PATENT DOCUMENTS

| | | |
|---|---|---|
| JP | 06-288903 A | 10/1994 |
| JP | 3049026 A | 3/1998 |
| JP | 2001-091447 A | 4/2001 |
| JP | 2002-139442 A | 5/2002 |

* cited by examiner

Fig. 21

| Item group | Specified item | Photoreceptive window | No.of light sources (lamps) |
|---|---|---|---|
| vegetable and fruit of large size | watermelon | large | 10 |
| | melon | large | 6 to 10 |
| vegetable and fruit of medium size | peach | medium | 6 |
| | apple | medium | 6 |
| | pear | medium | 4 to 6 |
| vegetable and fruit of small size | tangerine | small | 3 |
| | tomato | small | 2 or 3 |
| | mini tomato | small | 1 |

PRIOR ART

PRIOR ART

US 7,295,318 B2

APPARATUS AND METHOD FOR EVALUATING THE INTERIOR QUALITY OF FRUITS AND VEGETABLES

CROSS-REFERENCE TO RELATED APPLICATION

This application is a continuation of U.S. patent application Ser. No. 10/191,978 filed Jul. 9, 2002, now U.S. Pat. No. 7,151,606 entitled "Method for Evaluation of Vegetables and Fruits and Evaluation Apparatus Thereof" which is incorporated herein in its entirety.

BACKGROUND OF THE INVENTION

1. Field of the Invention

The present invention relates to an apparatus and a method for evaluation of vegetables and fruits which enable optically and nondestructively evaluating (measuring) the interior quality, such as sweetness degree (sugar content), acidity and maturity grade (ripening degree), of vegetables and fruits with the use of a carrier line.

2. Description of the Prior Art

Various techniques for measuring the interior quality, such as degree of sweetness (sugar content), acidity and maturity grade (ripening degree), of vegetables and fruits from the exterior without destroying them have been proposed.

As for the methods for nondestructively measuring the interior quality of vegetables and fruits, vegetables and fruits are irradiated with near infrared rays. In particular, the method of using reflection and the method of using a transmitted light have been proposed.

The method of using a reflected light is suitable to the measurement of, for example, peaches, pears and apples having a relatively thin epidermis. In this method, a measuring light (measuring beam), which has been transmitted through a thin epidermis, is reflected on a surface layer portion of sarcocarp, received by a light-receiving section. Then, the measuring light is analyzed so that measuring and evaluation of the interior quality of the above items can be achieved. However, in this method of using a reflected light, there is a drawback in that the light reflected on the vicinity of the surface layer portion or sarcocarp is received, so that only the interior quality of the vicinity of the epidermis can be identified by the analysis of obtained reflected light.

On the other hand, the evaluation method of using a transmitted light is suitable to the measurement of, for example, citrus fruits such as tangerines and oranges, melons and watermelons having a relatively thick epidermis. In this method, an irradiated measuring light is transmitted through the interior of sarcocarp and exits from the opposite side. Then, the irradiated measuring light is received by a light-receiving section and analyzed so that measuring and evaluation of the interior quality of the above items can be achieved. In this method of using a transmitted light, there is advantage that the light having been transmitted through the interior of sarcocarp of vegetables and fruits is analyzed, so that the properties of sarcocarp can be evaluated more accurately than in the method of using a reflected light. Therefore, the method of using a transmitted light is increasingly employed (see, for example, Japanese Registered Utility Model Publication No. 3049026 and Japanese Patent Laid-open Publication No. 2002-139442).

Evaluation apparatus 100 of single transmitted light type for vegetables and fruits, as shown in FIGS. 22 and 23, is heretofore in use as an evaluation apparatus of transmitted light type wherein a transmitted light is utilized as mentioned above.

Specifically, in this evaluation apparatus 100 for vegetables and fruits, light source 104 is disposed by one side of carrier line 102, such as a conveyor, in width direction Y perpendicular to carrying direction X of the carrier line 102. Further, light-receiving section 106 is disposed by the other side of the carrier line 102 in the width direction Y perpendicular to the carrying direction X of the carrier line 102. Thus, in this apparatus, a measuring light irradiated from the light source 104 is transmitted through the interior of sarcocarp of each of vegetables and fruits 108, and exits from the opposite side. Then, the measuring light is received by the light-receiving section 106 and is analyzed by a separate analyzer (not shown), so that measuring and evaluation of the interior quality of vegetables and fruits 108 can be achieved.

However, the above evaluation apparatus 100 for vegetables and fruits wherein a single light source 104 is disposed is in exclusive use, for example, for watermelons, or for tangerines. When, for example, tangerines having relatively small size, and small thickness of sarcocarp and pericarp (skin) are measured on a line for use in the measurement of, for example, watermelons having relatively large size, and large thickness of sarcocarp and pericarp, the quantity of light to be irradiated and the quantity of light to be received are too large so that accurate measurements cannot be expected. On the other hand, when contrarily watermelons are measured on a line for use in the measurement of tangerines, the light quantities are too small so that accurate measurements cannot be expected. That is, too large or too small light quantities cause the measurements to be inaccurate. Therefore, even when, for example, the watermelon line is free in the winter, it has been difficult to use the line for measurement of tangerines.

Moreover, only a diversion between watermelons and tangerines whose harvesting seasons are different could be coped with by purchasing two evaluation apparatuses and carrying out replacement of apparatuses in appropriate seasons. However, in the case of items whose harvesting seasons overlap, frequent replacements would be inevitable. Furthermore, when a variety of items are to be measured on a single line, the same number of evaluation apparatuses must be provided so that an enormous cost is incurred and further necessitates endeavoring to acquire storage sites.

Accordingly, as shown in FIGS. 24 and 25, evaluation apparatus of passing light type 200 for vegetables and fruits wherein a plurality of light sources are disposed in a horizontal direction so as to enable evaluation of vegetables and fruits having large size, and large thickness of sarcocarp and pericarp has been proposed.

In this evaluation apparatus 200 for vegetables and fruits, a plurality of horizontally arranged light sources 204a to 204e are disposed by one side of carrier line 202 in width direction Y perpendicular to carrying direction X of the carrier line 202. Further, light-receiving section 206 is disposed by the other side of the carrier line 202 in the width direction Y perpendicular to the carrying direction x of the carrier line 202. Thus, in this apparatus, as indicated by alternate long and two short dashes lines in FIG. 25, measuring lights irradiated from the light sources 204a to 204e are transmitted through the interior of sarcocarp of each of vegetables and fruits 208 and exits from the opposite side. Then, the measuring light is received by the light-receiving section 206 and is analyzed by a separate analyzer (not shown) so that measuring and evaluation of the interior quality of vegetables and fruits 208 can be achieved.

In the evaluation apparatus 200 for vegetables and fruits, a plurality of light sources 204a to 204e are employed as different from the aforementioned evaluation apparatus of single transmitted light type 100 for vegetables and fruits. Therefore, the evaluation apparatus 200 for vegetables and fruits enables increasing the number of transmitted lights, so that vegetables and fruits having relatively large size, and large thickness of sarcocarp and pericarp can be treated.

However, in this evaluation apparatus 200 for vegetables and fruits, vegetables and fruits 208 are moved on the carrier line 202 even during the measurement thereof, and a plurality of light sources 204a to 204e are arranged in a horizontal direction. Therefore, during the measurement of vegetables and fruits 208 being moved on the carrier line 202, especially at the beginning or ending of measurement, it has unfavorably occurred that the light-receiving section 206 receives lights from the periphery of vegetables and fruits 208 other than the intended transmitted lights, such as straight lights from the peripherally arranged light sources, for example, light sources 204a to 204e, reflected lights from vegetables and fruits 208 and reflected lights from neighboring vegetables and fruits 208. As a result, the accuracy of measuring evaluation is deteriorated.

This phenomenon can be avoided by shortening the measuring time. However, generally, the accuracy of measuring evaluation would be deteriorated by shortening of the measuring time.

With respect to the evaluation apparatus of single transmitted light type 100 for vegetables and fruits, single light source 104 is used, so that this phenomenon is relatively slight. However, receiving of such lights other than the intended transmitted light cannot be fully avoided.

Furthermore, in the evaluation apparatus 200 for vegetables and fruits, although vegetables and fruits having relatively large size, and large thickness of sarcocarp and pericarp thickness can be treated, accurate measuring of vegetables and fruits having relatively small size and small thickness of sarcocarp and pericarp cannot be realized because the quantity of light to be irradiated and the quantity of light to be received are too intense.

Under these circumstances, it is an object of the present invention to provide an evaluation apparatus for vegetables and fruits and an evaluation method for vegetables and fruits which, in the measuring of vegetables and fruits being moved on a carrier line, enable realizing accurate measuring evaluation with strikingly enhanced precision while avoiding the receiving, by a light-receiving section, of lights from the periphery of vegetables and fruits other than intended transmitted lights, such as straight lights from light sources, reflected lights from vegetables and fruits and reflected lights from neighboring vegetables and fruits.

It is another object of the present invention to provide an evaluation apparatus for vegetables and fruits and an evaluation method for vegetables and fruits which enable realizing accurate measuring evaluation with strikingly enhanced precision with respect to vegetables and fruits having widely varied size and varied thickness of sarcocarp and pericarp as well.

SUMMARY OF THE INVENTION

The present invention has been made with a view toward solving the above drawbacks of the prior art and attaining the above objects. Therefore, according to an aspect of the present invention, there is provided an evaluation apparatus for vegetables and fruits capable of evaluating vegetables and fruits with respect to their interior quality through exposing vegetables and fruits carried on a carrier line to measuring lights irradiated from light sources so as to have the measuring lights transmitted through the vegetables and fruits and causing a light-receiving section to receive the transmitted measuring lights, which evaluation apparatus comprises:

a plurality of light sources vertically arranged by one side of a carrier line in width direction Y perpendicular to carrying direction X of the carrier line; and a light-receiving section arranged by an opposite side of the carrier line in the width direction Y perpendicular to the carrying direction X of the carrier line.

In another aspect of the present invention, there is provided a method for evaluation of vegetables and fruits including exposing vegetables and fruits carried on a carrier line to measuring lights irradiated from light sources so as to have the measuring lights transmitted through the vegetables and fruits and causing a light-receiving section to receive the transmitted measuring lights to thereby enable evaluation of the vegetables and fruits with respect to their interior quality, which method comprises:

exposing vegetables and fruits to measuring lights irradiated from a plurality of light sources vertically arranged by one side of a carrier line in width direction Y perpendicular to carrying direction X of the carrier line; and causing a light-receiving section arranged by an opposite side of the carrier line in the width direction Y perpendicular to the carrying direction X of the carrier line to receive measuring lights having been transmitted through the vegetables and fruits to thereby enable evaluation of the vegetables and fruits with respect to their interior quality.

In the above construction, vegetables and fruits are exposed to measuring lights irradiated from a plurality of light sources vertically arranged by one side of a carrier line in the width direction Y perpendicular to the carrying direction X of the carrier line. Therefore, during the measurement of vegetables and fruits being moved on the carrier line, especially at the beginning or ending of measurement, the light-receiving section does not receive any lights from the periphery of vegetables and fruits other than the intended transmitted lights, such as straight lights from the light sources, reflected lights from vegetables and fruits and reflected lights from neighboring vegetables and fruits. As a result, the accuracy of measuring evaluation is strikingly enhanced and an accurate measuring evaluation can be realized.

The present invention is preferably characterized in that the plurality of vertically arranged light sources are disposed so that an angle α from the width direction Y perpendicular to the carrying direction X of the carrier line is in the range of 90° or less.

When the plurality of vertically arranged light sources are disposed so that an angle α from the width direction Y perpendicular to the carrying direction X of the carrier line is in the range of 90° or less, only lights having been transmitted through the vegetables and fruits are received by the light-receiving section. Therefore, receiving of reflected lights from the vegetables and fruits, etc. by the light-receiving section can be avoided. As a result, the accuracy of measuring evaluation can be further enhanced and an accurate measuring evaluation can be realized.

Further, the evaluation apparatus for vegetables and fruits according to the present invention is preferably characterized in that a shading plate is interposed between the light sources and the light-receiving section, the shading plate being capable of shading lights other than the measuring lights transmitted through vegetables and fruits so as to avoid receiving of lights other than the measuring lights having been transmitted through vegetables and fruits by the light-receiving section.

Also, the method for evaluation of vegetables and fruits according to the present invention is preferably characterized in that lights other than the measuring lights transmitted through vegetables and fruits are shaded so as to avoid receiving of lights other than the measuring lights having been transmitted through vegetables and fruits by the light-receiving section.

In the above construction, the shading plate arranged between the light sources and the light-receiving section shades any lights from the periphery of vegetables and fruits other than the intended lights having been transmitted through vegetables and fruits, such as straight lights from the light sources, reflected lights from vegetables and fruits and reflected lights from neighboring vegetables and fruits. Therefore, receiving of any lights other than the intended lights having been transmitted through vegetables and fruits by the light-receiving section can be avoided. As a result, the accuracy of measuring evaluation can be further enhanced and an accurate measuring evaluation can be realized.

Still further, the present invention is preferably characterized in that the shading plate comprises shading plate members disposed in parallel with the carrying direction X of the carrier line.

In the above construction, any lights from the periphery of vegetables and fruits other than the intended lights having been transmitted through vegetables and fruits, such as straight lights from the light sources, reflected lights from vegetables and fruits and reflected lights from neighboring vegetables and fruits, are shaded by the shading plate members disposed in parallel with the carrying direction X of the carrier line. Therefore, receiving of any lights other than the intended lights having been transmitted through vegetables and fruits by the light-receiving section can be avoided. As a result, the accuracy of measuring evaluation can be further enhanced and an accurate measuring evaluation can be realized.

Still further, the present invention is preferably characterized in that the shading plate comprises a plurality of shading plate members disposed in parallel with the carrying direction X of the carrier line, the plurality of shading plate members being arranged in parallel relationship with given spacings in the width direction Y of the carrier line.

In the above construction, the plurality of shading plate members efficiently shade any lights from the periphery of vegetables and fruits other than the intended lights having been transmitted through vegetables and fruits, such as straight lights from the light sources, reflected lights from vegetables and fruits and reflected lights from neighboring vegetables and fruits. As a result, the accuracy of measuring evaluation can be further enhanced and an accurate measuring evaluation can be realized.

The present invention is, still further, preferably characterized in that the plurality of shading plate members arranged in parallel relationship with given spacings in the width direction Y of the carrier line have lengths which are those having lower end portions along an outline of vegetables and fruits.

In the above construction, a tunnellike passage route for vegetables and fruits along the outline of vegetables and fruits is formed in the carrying direction X of the carrier line. Thus, the vegetables and fruits carried on the carrier line are not damaged by shading plate members. Furthermore, the shading plate members have no influence upon the position and posture of vegetables and fruits on the carrier line, so that the accuracy of measuring evaluation can be enhanced and an accurate measuring evaluation can be realized.

Also, the light-receiving section does not receive any lights from the periphery of vegetables and fruits other than the intended transmitted lights through vegetables and fruits, such as straight lights from the light sources, reflected lights from vegetables and fruits and reflected lights from neighboring vegetables and fruits, through any gap between the lower end portions of shading plate members and the vegetables and fruits. As a result, the accuracy of measuring evaluation can be further enhanced and an accurate measuring evaluation can be realized.

Moreover, the present invention is preferably characterized in that the shading plate comprises side shading plate members arranged in the width direction Y perpendicular to the carrying direction X of the carrier line.

In the above construction, reflected lights from neighboring vegetables and fruits can be shaded by the side shading plate members. Further, the side shading plate members define an irradiation path of measuring lights from the light sources. Thus, any lights other than the lights having been transmitted through the vegetables and fruits can be efficiently shaded so that the accuracy of measuring evaluation can be further enhanced and an accurate measuring evaluation can be realized.

The present invention is also preferably characterized in that the shading plate comprises an upper shading plate member of configuration along an upper outline of vegetables and fruits.

In the above construction, by virtue of the upper shading plate member, the light-receiving section does not receive any lights from the periphery of vegetables and fruits other than the intended transmitted lights through vegetables and fruits, such as straight lights from the light sources, reflected lights from vegetables and fruits and reflected lights from neighboring vegetables and fruits. As a result, the accuracy of measuring evaluation can be further enhanced and an accurate measuring evaluation can be realized.

Also, a tunnel-like passage route for vegetables and fruits along the outline of vegetables and fruits is formed in the carrying direction X of the carrier line. Thus, the vegetables and fruits carried on the carrier line by shading plate members are not damaged. Furthermore, the shading plate members have no influence upon the position and posture of vegetables and fruits on the carrier line so that the accuracy of measuring evaluation can be enhanced and an accurate measuring evaluation can be realized.

Further, the present invention is preferably characterized in that the shading plate is provided with slits for enabling exposure of the vegetables and fruits to the measuring lights from the light sources.

In the above construction, measuring lights irradiated from the light sources can pass through slits provided in the shading plate to vegetables and fruits without being shaded by the shading plate members. As a result, the lights having been transmitted through the vegetables and fruits can be efficiently received by the light-receiving section. Thus, the accuracy of measuring evaluation can be enhanced, and an accurate measuring evaluation can be realized.

Still further, the present invention is preferably characterized in that the shading plate is so constructed to be vertically movable in accordance with sizes of vegetables and fruits.

In the above construction, even when the size of vegetables and fruits is varied, lights other than the lights having been transmitted through the vegetables and fruits can be efficiently shaded by the shading plate. As a result, the accuracy of measuring evaluation can be enhanced and an accurate measuring evaluation can be realized.

Still further, the present invention is preferably characterized in that the plurality of vertically arranged light sources are so constructed as to permit selection of light sources for irradiating measuring lights toward vegetables and fruits in accordance with sizes and types of vegetables and fruits.

In the above construction, the quantities of measuring lights and transmitted lights can be regulated with respect to vegetables and fruits having widely varied size, and varied thickness of sarcocarp and pericarp as well. Thus the accuracy of measuring evaluation can be enhanced and an accurate measuring evaluation can be realized.

In a further aspect of the present invention, there is provided an evaluation apparatus for vegetables and fruits capable of evaluating vegetables and fruits with respect to their interior quality through exposing vegetables and fruits carried on a carrier line to measuring lights irradiated from light sources so as to have the measuring lights transmitted through the vegetables and fruits and causing a light-receiving section to receive the transmitted measuring lights, which evaluation apparatus comprises:

a plurality of light sources capable of irradiating measuring lights of given quantity;

means for regulating the quantity of measuring lights from the light sources in accordance with sizes of vegetables and fruits;

a light-receiving window of given openness provided in a carrier line, the light-receiving window being capable of leading measuring lights having been transmitted through the vegetables and fruits toward a light-receiving section; and means for regulating quantities of transmitted light provided to the light-receiving window, the means for regulating quantities of transmitted light being capable of regulating the openness of the light-receiving window.

In still a further aspect of the present invention, there is provided a method for evaluation of vegetables and fruits including exposing vegetables and fruits carried on a carrier line to measuring lights irradiated from light sources so as to have the measuring lights transmitted through the vegetables and fruits and causing a light-receiving section to receive the transmitted measuring lights to thereby enable evaluating the vegetables and fruits with respect to their interior quality, which method comprises:

arranging a plurality of light sources capable of irradiating measuring lights of given quantity, and regulating the quantity of measuring lights from the light sources in accordance with sizes of vegetables and fruits; and providing a carrier line with not only a light-receiving window of given openness, the light-receiving window being capable of leading measuring lights having been transmitted through the vegetables and fruits toward a light-receiving section, and providing a carrier line with means for regulating quantities of transmitted light, the means for regulating quantities of transmitted light being capable of regulating the openness of the light-receiving window, and whereby a measuring evaluation of the vegetables and fruits is performed while regulating quantities of the transmitted light received by the light-receiving section with the use of the means for regulating quantities of transmitted light.

In the above construction, the quantity of measuring lights from the light sources can be regulated by the plurality of arranged light sources in accordance with the size of vegetables and fruits. Furthermore, the quantity of transmitted lights received by the light-receiving section can be regulated by regulating the openness of the light-receiving window with the use of the means for regulating quantity of transmitted light. Thus, the quantity of measuring lights and the quantity of transmitted lights can be regulated appropriately and simply in accordance with the size of vegetables and fruits. Therefore, the evaluation of vegetables and fruits of varied item species and sizes can be accomplished on a single carrier line with economic advantage.

The present invention is preferably characterized in that the regulation of the quantity of measuring lights from the light sources is performed by controlling the number of lit light sources.

In the above construction, the quantity of measuring lights can be regulated without changing the intensity of individual light sources (lamps), so that the regulation of lights transmitted through vegetables and fruits can be appropriately performed.

Further, the present invention is preferably characterized in that the light sources comprise:

upper light sources capable of irradiating measuring lights toward vegetables and fruits from overhead when carried vegetables and fruits pass a given measuring point; and side light sources capable of irradiating measuring lights toward the vegetables and fruits from right and left sides.

In the above construction, the upper light sources and the side light sources irradiate measuring lights toward the vegetables and fruits from overhead and right and left sides, respectively, so that the interior quality of vegetables and fruits can be measured with high accuracy.

Still further, the present invention is preferably characterized in that a plurality of upper light sources are arranged in a row in right and left direction Y perpendicular to carrying direction X of the carrier line.

In the above construction, the plurality of upper light sources arranged in a row in the right and left direction Y perpendicular to the carrying direction X of the carrier line evenly irradiate measuring lights toward vegetables and fruits from overhead, so that the interior quality of vegetables and fruits can be measured with high accuracy.

Still further, the present invention is preferably characterized in that the side light sources are arranged in dispersion on the circumference of a circle centering on the measuring point.

In the above construction, the side light sources arranged in dispersion on the circumference of a circle evenly irradiate measuring lights toward vegetables and fruits from lateral sides, so that the interior quality of vegetables and fruits can be measured with high accuracy.

BRIEF DESCRIPTION OF THE DRAWINGS

FIG. 21 is a table showing a pattern of combination between the openness of light-receiving window and the number of lit light sources according to the size and item species of vegetables and fruits;

DETAILED DESCRIPTION OF THE INVENTION

Hereinbelow, various embodiments (working examples) of the present invention will be described in greater detail with reference to the appended drawings.

Figure 1:
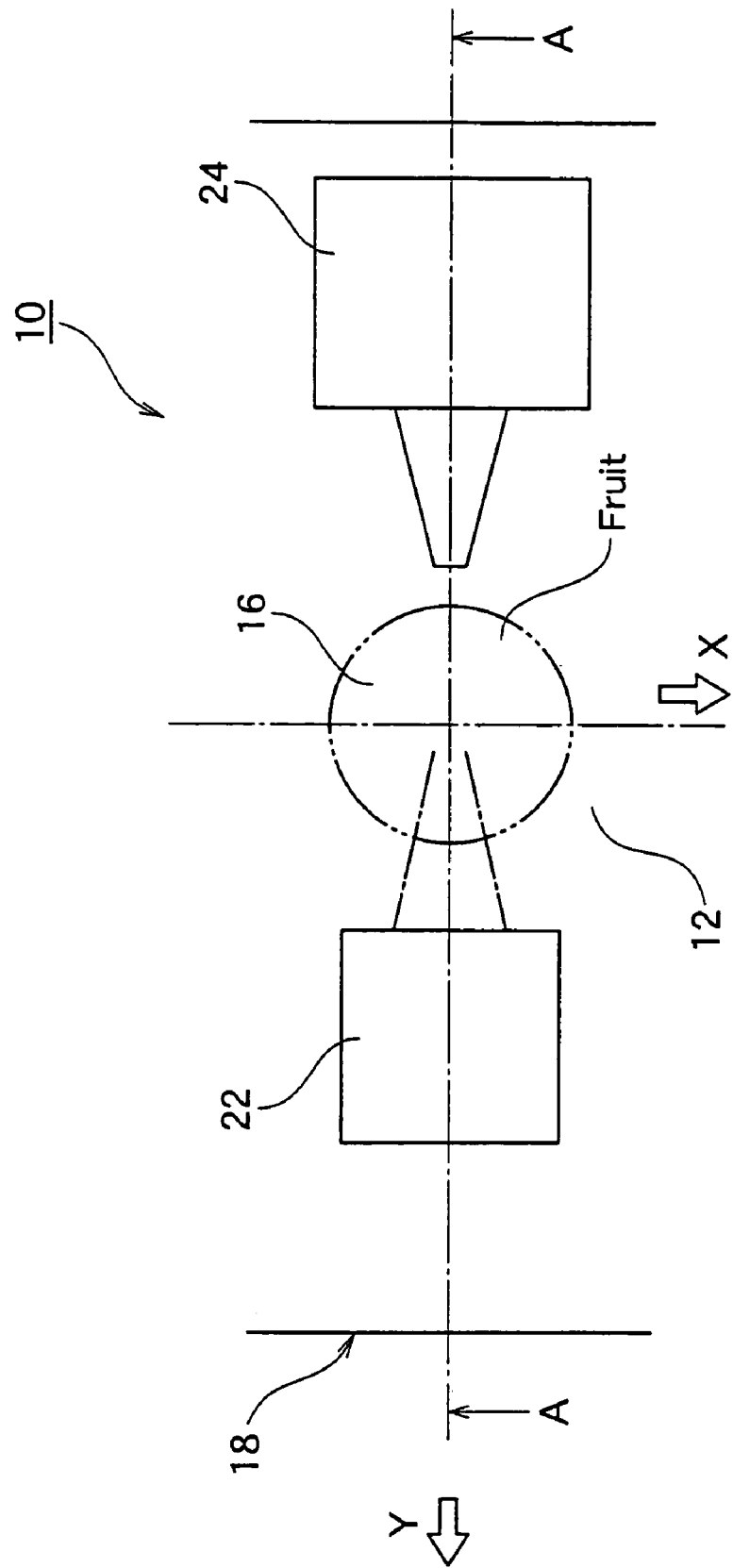
FIG. 1 is a top view of the first form of evaluation apparatus for vegetables and fruits according to the present invention.

FIG. 1 is a top view of the first form of evaluation apparatus for vegetables and fruits according to the present invention.

Figure 2:
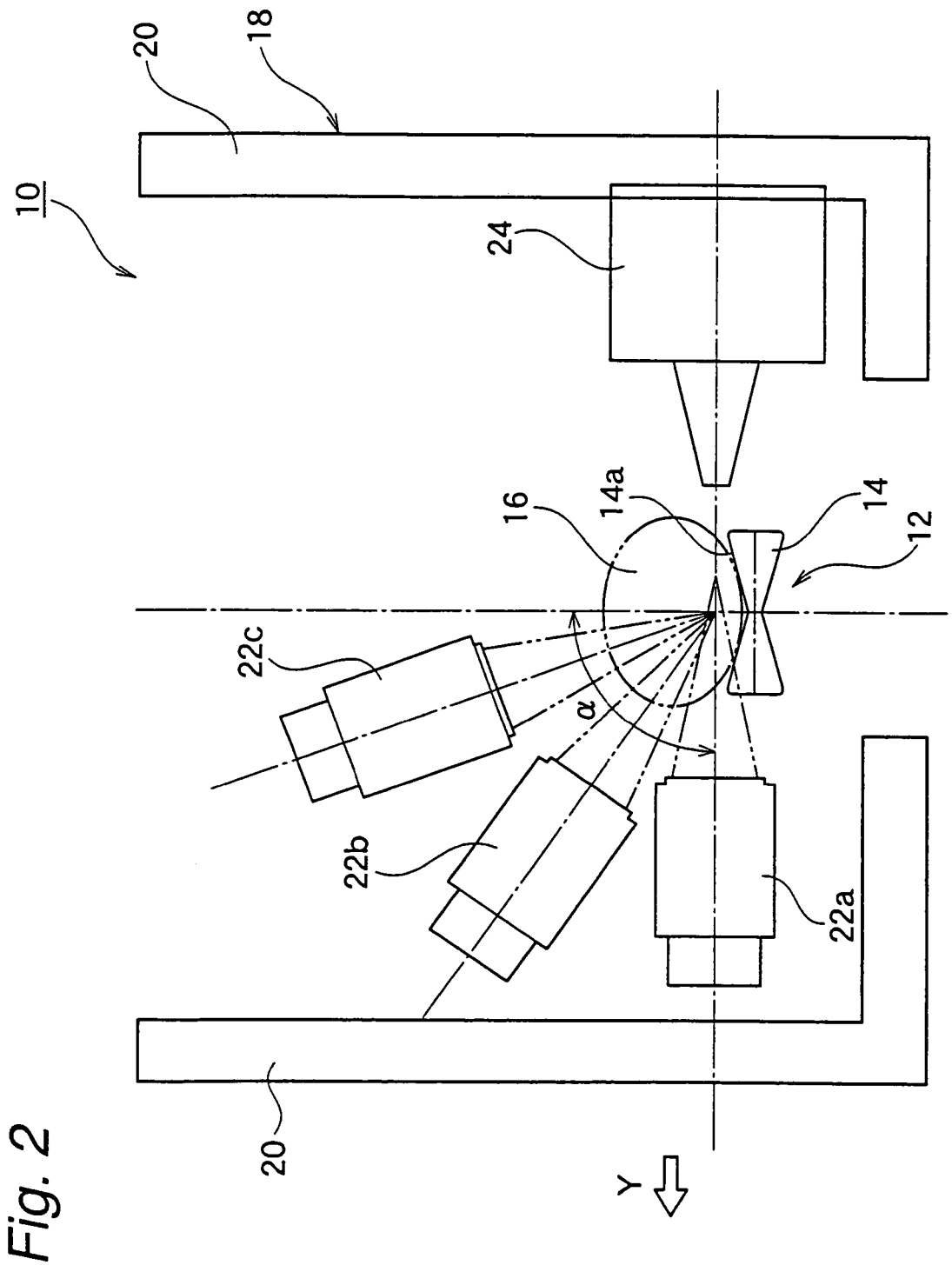
FIG. 2 is a view of section line A-A of FIG. 1.

FIG. 2 is a view of section line A-A of FIG. 1.

In FIG. 1, numeral 10 generally denotes one form of evaluation apparatus for vegetables and fruits according to the present invention (hereinafter simply referred to as "evaluation apparatus").

As shown in FIGS. 1 and 2, the following first to fourth forms of evaluation apparatuses are such types of evaluation apparatuses wherein measuring evaluation of vegetables and fruits is carried out by disposing light sources in a vertical direction by one side of vegetables and fruits and simultaneously disposing a light-receiving section by another side of vegetables and fruits which is opposite to the light sources.

As shown in FIGS. 1 and 2, the evaluation apparatus 10 includes carrier trays 14 placed on carrier line 12 (for example, conveyor) with given spacings in sequence in carrying direction X. The upper side of each of the carrier trays 14 has outward sloped taper surface 14a. On this taper surface 14a, each of vegetables and fruits 16 such as tangerines and apples to be evaluated is mounted, so that the vegetables and fruits 16 are conveyed in the carrying direction X in sequence.

Evaluation apparatus section 18 is provided along the carrier line 12. The evaluation apparatus section 18 includes frame 20 provided so as to surround the carrier line 12.

Light source 22 is disposed by one side of the carrier line 12 in width direction Y perpendicular to the carrying direction X of the carrier line 12. This light source 22 includes a plurality of light sources 22a to 22c (in this form of evaluation apparatus, three light sources) arranged vertically with given spacings.

Further, light-receiving section 24 is disposed by the other side of the carrier line 12 in the width direction Y perpendicular to the carrying direction X of the carrier line 12.

Thus, in such a construction, as indicated by alternate long and short dash lines in FIGS. 1 and 2, measuring lights (near infrared lights) irradiated from the light sources 22a to 22c are transmitted through the interior of sarcocarp of each of vegetables and fruits 16, and the measuring light exits from the opposite side. Then, the measuring light is received by the light-receiving section 24 and analyzed by a separate analyzer (not shown) so that measuring evaluation of the interior quality of vegetables and fruits 16 can be achieved.

That is, the transmitted lights having exited from the vegetables and fruits 16 exhibit absorption spectra which are different depending on the characteristics of each of the vegetables and fruits 16. The spectral data are compared with the data inputted in advance in the analyzer on the basis of prior measurements of the interior quality, such as sweetness degree, acidity and maturity grade, of vegetables and fruits, so that evaluation of the interior quality of vegetables and fruits 16 can be achieved.

In this construction, the vegetables and fruits 16 are exposed to measuring lights irradiated from the plurality of light sources 22a to 22c vertically arranged by one side of the carrier line 12 in the width direction Y perpendicular to the carrying direction X of the carrier line 12.

Therefore, during the measurement of vegetables and fruits 16 being moved on the carrier line 12, especially at the beginning or ending of measurement, the light-receiving section 24 does not receive any lights from the periphery of vegetables and fruits 16 other than the intended transmitted lights, such as straight lights from the light sources 22a to 22c, reflected lights from vegetables and fruits 16 and reflected lights from neighboring vegetables and fruits 16. As a result, the accuracy of measuring evaluation can be strikingly enhanced and an accurate measuring evaluation can be realized.

In this construction, it is preferred that, as shown in FIG. 1, the plurality of vertically arranged light sources 22a to 22c should be disposed so that an angle α from the width direction Y perpendicular to the carrying direction X of the carrier line 12 is in the range of 90° or less.

When the plurality of vertically arranged light sources 22a to 22c are disposed so that an angle α from the width direction Y perpendicular to the carrying direction X of the carrier line 12 is in the range of 90° or less, as shown in FIG. 1, reflection of measuring lights irradiated from the light sources 22a to 22c by the vegetables and fruits 16 cannot be received by the light-receiving section 24. Therefore, only lights having been transmitted through the vegetables and fruits 16 are received by the light-receiving section 24.

Thus, receiving of reflected lights from the vegetables and fruits 16 by the light-receiving section 24 can be avoided, so that the accuracy of measuring evaluation can be further enhanced and an accurate measuring evaluation can be realized.

In this construction, the number of light sources 22a to 22c and positions of arrangement thereof are not particularly limited as long as the angle α falls within the above range, and can be appropriately selected depending on the type, size, etc. of vegetables and fruits 16.

By virtue of the arrangement of the plurality of light sources 22a to 22c, satisfactory quantities of measuring light and transmitted light can be ensured for the vegetables and fruits having large size and large thickness of sarcocarp and pericarp as well, so that accurate measuring evaluation can be realized.

In the irradiation of measuring lights from the light sources 22a to 22c, it is preferred to regulate quantities of the light in accordance with the transmission ratio depending on the type of vegetables and fruits 16 and size thereof. The regulation of quantities of irradiated light can be accomplished by such a construction that a control unit (not shown) changes the number of lit light sources 22a to 22c in accordance with the type and size of vegetables and fruits 16. For example, only one light source lit for vegetables and fruits 16 of small diameter such as tangerines and tomatoes; two light sources lit for vegetables and fruits 16 of medium size such as peaches and apples; and three light sources lit for vegetables and fruits 16 of large size such as watermelons and melons.

Further, in the regulation of the number of lit light sources, lighting of the light sources 22a to 22c may be performed in such a manner that, for example, every second one or every third one is lit so as to enable exposure of the vegetables and fruits 16 to measuring lights at varied angles. Also, the light sources 22a to 22c may be designed so that the angles (directions) thereof are changeable in accordance with the size of vegetables and fruits 16 to thereby enable converging of measuring lights on the center of each of vegetables and fruits 16.

Figure 3:
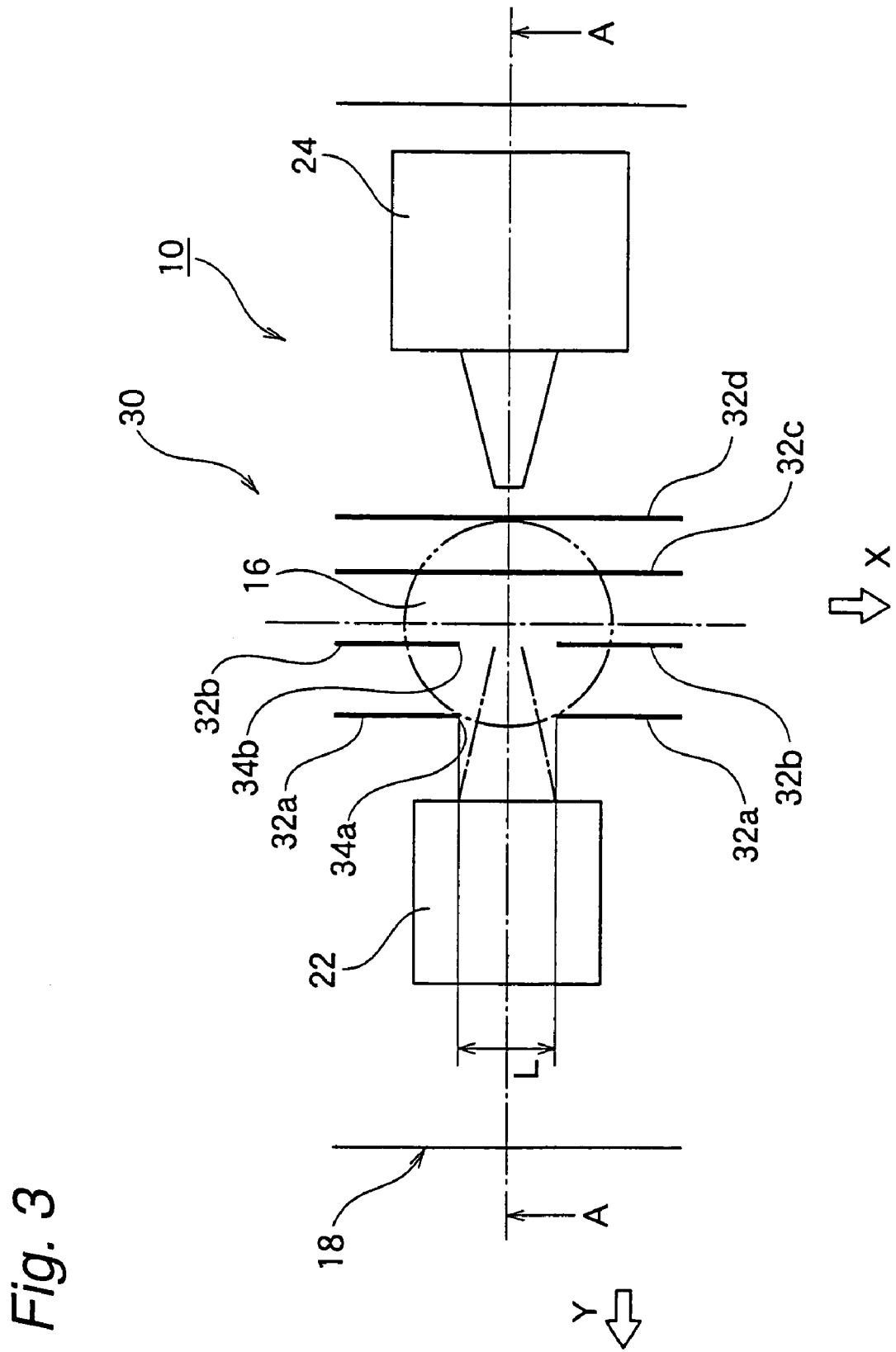
FIG. 3 is a top view of the second form of evaluation apparatus for vegetables and fruits according to the present invention.
Figure 4:
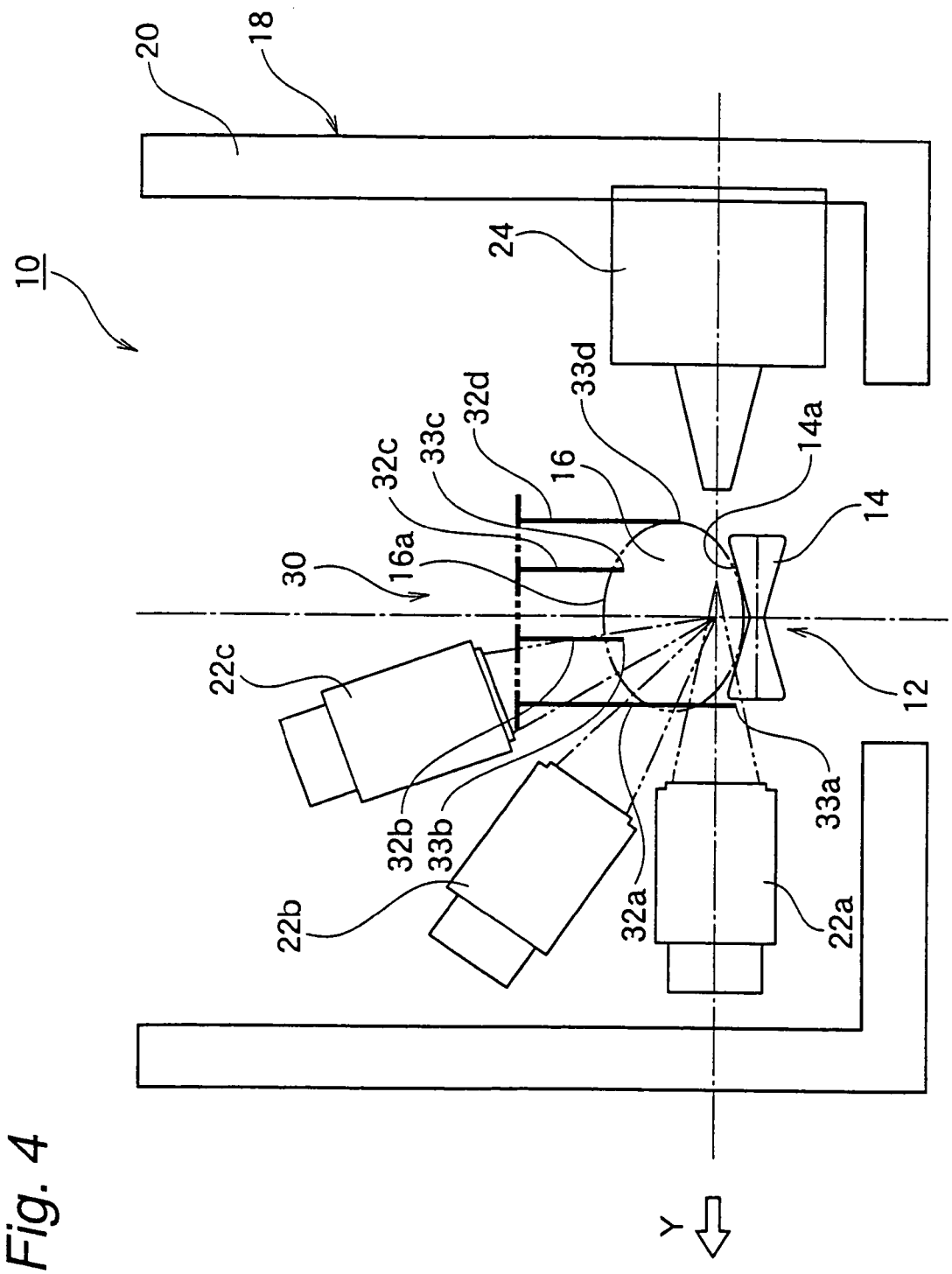
FIG. 4 is a view of section line A-A of FIG. 3.
Figure 5:
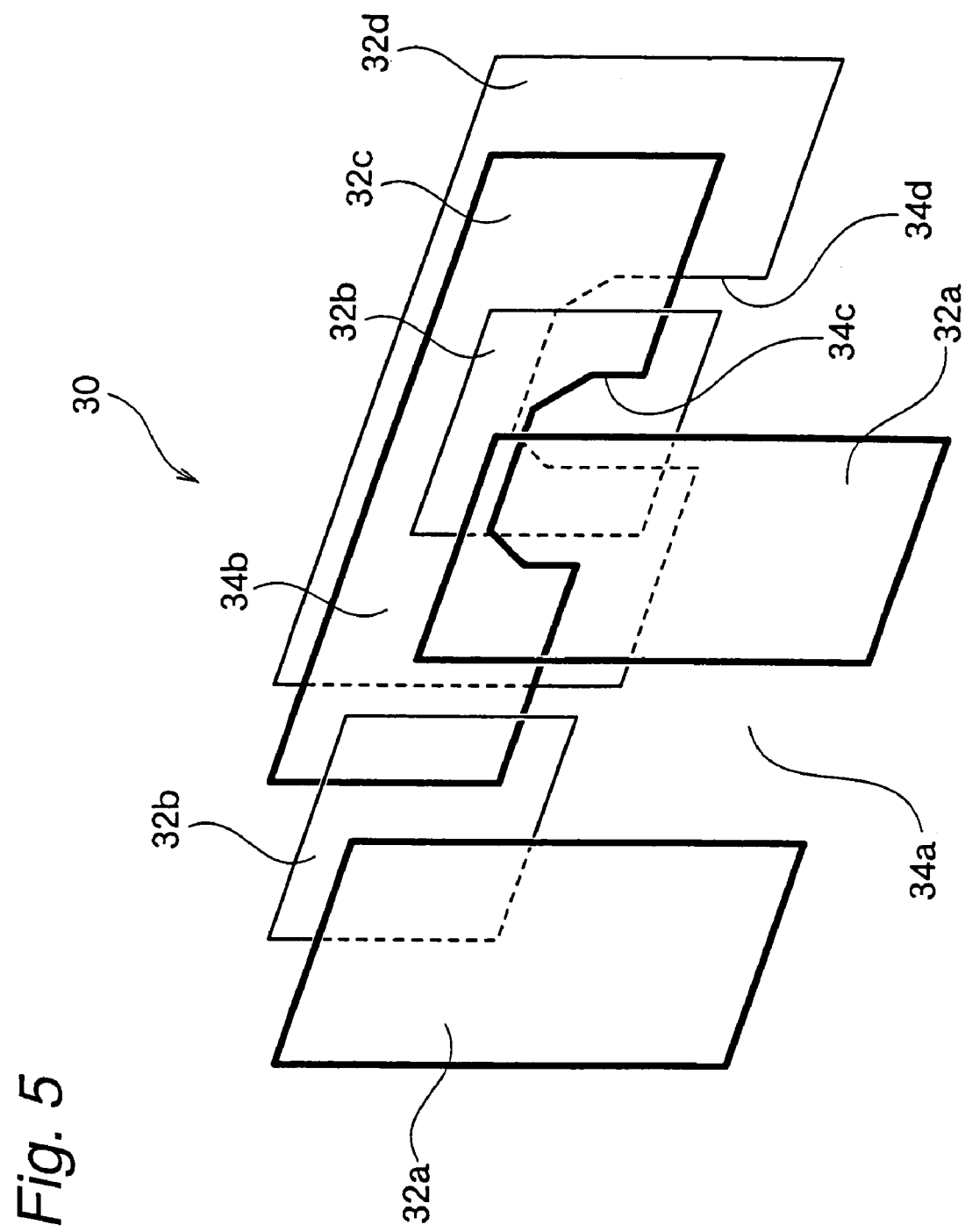
FIG. 5 is an enlarged perspective view of a shading plate.

FIG. 3 is a top view of the second form of evaluation apparatus for vegetables and fruits according to the present invention. FIG. 4 is a view of section line A-A of FIG. 3. FIG. 5 is an enlarged perspective view of a shading plate.

The construction of this form of evaluation apparatus 10 is fundamentally the same as that of the evaluation apparatus 10 shown in FIGS. 1 and 2. Like reference numerals are used for like constituent members, and detailed description thereof will be omitted.

In this form of evaluation apparatus 10, shading plate 30 capable of shading lights other than the lights transmitted through vegetables and fruits 16 is disposed between the light sources 22a to 22c and the light-receiving section 24 over the carrier line 12, so that lights other than the lights having been transmitted through vegetables and fruits 16 are not received by the light-receiving section 24.

This shading plate 30, in this form of evaluation apparatus 10, is disposed in parallel with the carrying direction X of the carrier line 12, and is provided with a plurality of shading plate members 32 arranged in parallel relationship with given spacings in the width direction Y of the carrier line 12.

Specifically, in this form of evaluation apparatus 10, four shading plate members 32a to 32d, which are arranged from the side of light source 22, are disposed in parallel relationship with given spacings in the width direction Y of the carrier line 12 over the carrier line 12 and secured by holddown members (not shown), so that the shading plate members 32a to 32d are positioned on a line binding the light source 22 and the light-receiving section 24.

Further, as shown in FIGS. 3 to 5, the shading plate 30 is so constructed that the lengths of shading plate members 32a to 32d are those having lower end portions 33a to 33d along the outline of each of vegetables and fruits 16, respectively.

From the viewpoint of preventing damaging of the vegetables and fruits 16 carried on the carrier line 12 by the shading plate members 32a to 32d, it is preferred that the lower end portions 33a to 33d of the shading plate members 32a to 32d should be positioned so as to make the lengths of shading plate members 32a to 32d those along the outline of vegetables and fruits 16, or slightly smaller than the outline of vegetables and fruits 16.

Furthermore, as shown in FIGS. 4 and 5, the shading plate members 32a to 32d are respectively provided with slits 34a to 34d for permitting transmission of measuring lights from the light source 22 through vegetables and fruits 16.

The width L of each of the slits 34a to 34d can be appropriately set in accordance with, for example, the size of vegetables and fruits 16 and the quantity of measuring lights irradiated from the light sources 22a to 22c, and is not particularly limited.

In this construction, the plurality of shading plate members 32a to 32d disposed in parallel with the carrying direction X of the carrier line 12 and arranged in parallel relationship with given spacings in the width direction Y of the carrier line 12 effectively shade lights from the periphery of vegetables and fruits 16 other than the intended transmitted lights through vegetables and fruits 16, such as straight lights from the light sources 22a to 22c, reflected lights from vegetables and fruits 16 and reflected lights from neighboring vegetables and fruits 16.

Accordingly, receiving of lights other than the lights transmitted through vegetables and fruits 16 by the light-receiving section 24 can be avoided, so that the accuracy of measuring evaluation can be further enhanced and an accurate measuring evaluation can be realized.

Because the lengths of shading plate members 32a to 32d are those having lower end portions 33a to 33d along the outline of each of vegetables and fruits 16, respectively, a tunnellike passage route for vegetables and fruits 16 along the outline of vegetables and fruits 16 is formed in the carrying direction X of the carrier line 12. Thus, damaging of the vegetables and fruits 16 carried on the carrier line 12 by the shading plate members 32a to 32d can be avoided. Further, the shading plate members 32a to 32d have no influence upon the position and posture of vegetables and fruits 16 on the carrier line 12, so that the accuracy of measuring evaluation can be enhanced and an accurate measuring evaluation can be realized.

Moreover, the light-receiving section 24 does not receive any lights from the periphery of vegetables and fruits 16 other than the intended transmitted lights through vegetables and fruits 16, such as straight lights from the light sources 22a to 22c, reflected lights from vegetables and fruits 16 and reflected lights from neighboring vegetables and fruits 16, through any gap between the lower end portions 33a to 33d of shading plate members 32a to 32d and the vegetables and fruits 16 can be avoided. As a result, the accuracy of measuring evaluation can be further enhanced and an accurate measuring evaluation can be realized.

Furthermore, because the shading plate members 32a to 32d are respectively provided with the slits 34a to 34d for permitting transmission of measuring lights from the light source 22 through vegetables and fruits 16, any measuring lights from the light sources 22a to 22c are not shaded by the shading plate members 32a to 32d. Also, through the slits 34a to 34d of the shading plate members 32a to 32d, exposure of the vegetables and fruits 16 to measuring lights is ensured and the measuring light is transmitted through the vegetables and fruits 16 and transmitted lights can be efficiently received by the light-receiving section 24. As a result, the accuracy of measuring evaluation can be further enhanced and an accurate measuring evaluation can be realized.

As long as the shading plate members 32a to 32d are constituted of a soft material which can shade measuring lights irradiated from the light sources 22a to 22c in order to avoid any damaging of the vegetables and fruits 16 carried on the carrier line 12 and to avoid any influence upon the position and posture of vegetables and fruits 16 on the carrier line 12, the materials of the shading plate members 32a to 32d are not particularly limited. For example, the shading plate members 32a to 32d can be made of rubber, cloth or synthetic resin films. Further, although not shown, the shading plate members 32a to 32d can be constituted of, for example, a material having like a reed screen configuration.

Still further, the shading plate 30 is preferably so constructed as to be vertically movable by, for example, driving means such as a servomotor, not shown, in accordance with the type and size of vegetables and fruits 16. When this construction is made, even if the size of vegetables and fruits 16 is varied, lights other than the lights transmitted through the vegetables and fruits 16 can be efficiently shaded by the shading plate 30. Thus, the accuracy of measuring evaluation can be enhanced and an accurate measuring evaluation can be realized.

Figure 6:
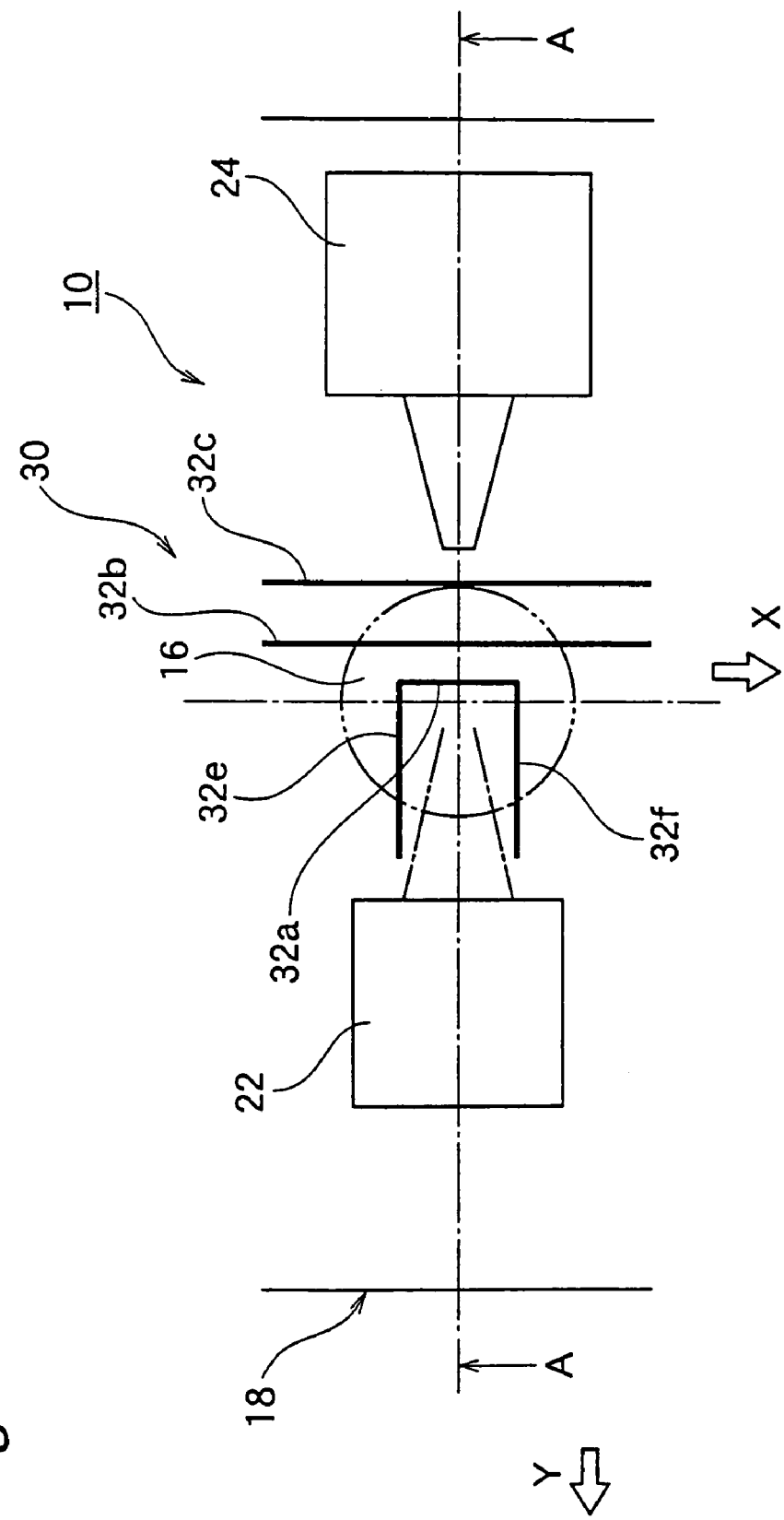
FIG. 6 is a top view of the third form of evaluation apparatus for vegetables and fruits according to the present invention.
Figure 7:
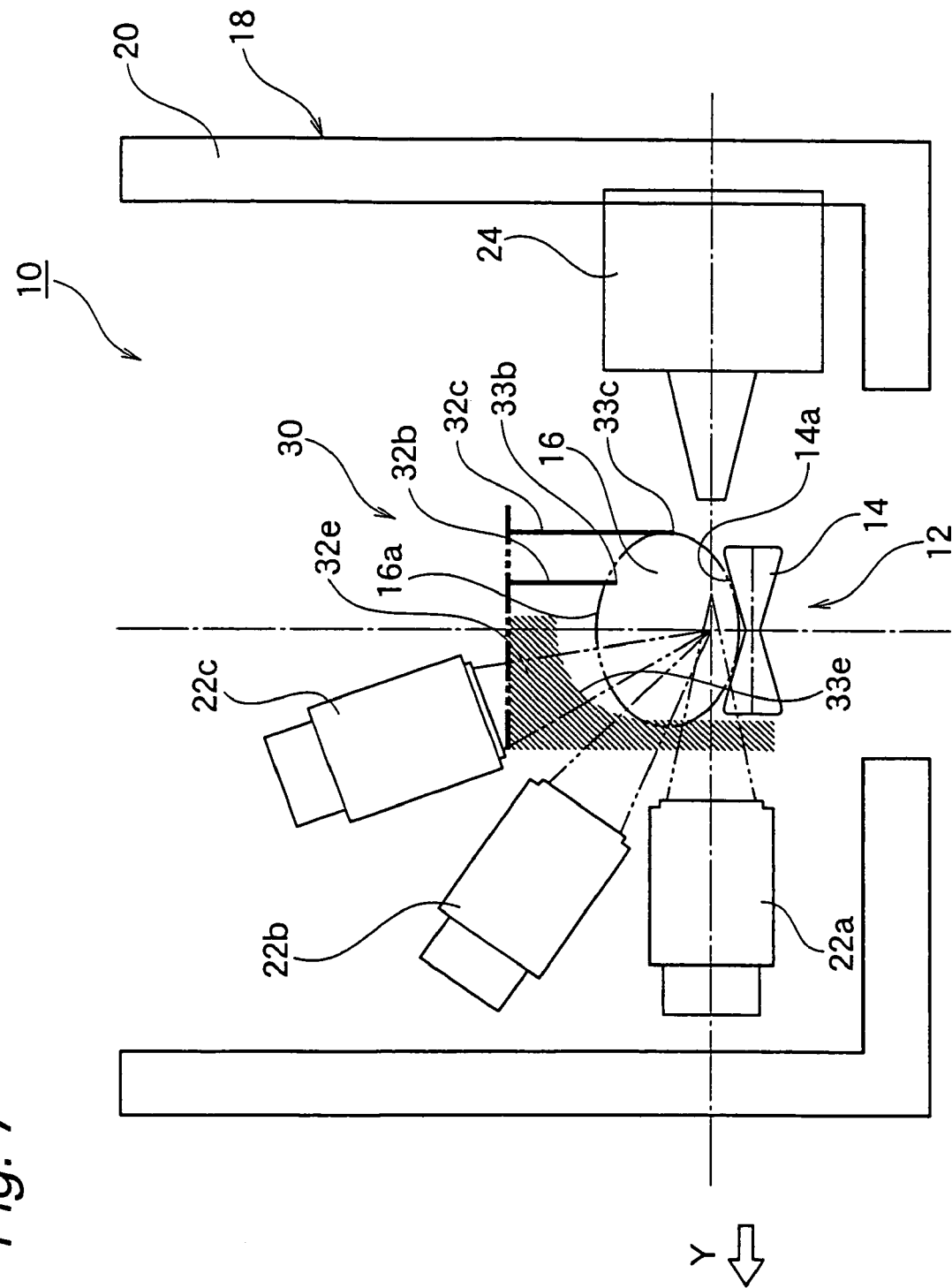
FIG. 7 is a view of section line A-A of FIG. 6.
Figure 8:
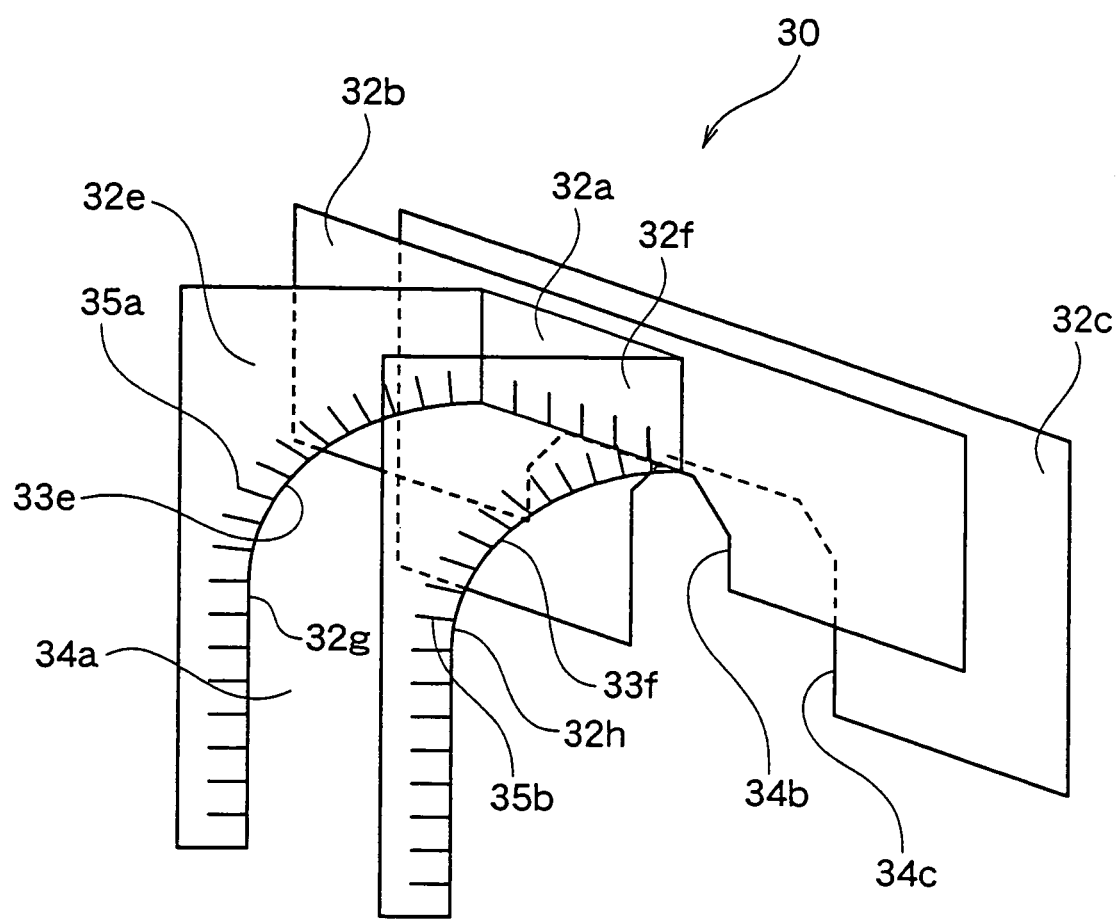
FIG. 8 is an enlarged perspective view of a shading plate.

FIG. 6 is a top view of the third form of evaluation apparatus for vegetables and fruits according to the present invention. FIG. 7 is a view of section line A-A of FIG. 6. FIG. 8 is an enlarged perspective view of a shading plate.

The construction of this form of evaluation apparatus 10 is fundamentally the same as that of the second form of evaluation apparatus 10 shown in FIGS. 3 to 5. Like reference numerals are used for like constituent members, and detailed description thereof will be omitted.

In this form of evaluation apparatus 10, the shading plate 30 is disposed in parallel with the carrying direction X of the carrier line 12, and is provided with a plurality (in this form of evaluation apparatus 10, three) of shading plate members 32a to 32c arranged in parallel relationship with given spacings in the width direction Y of the carrier line 12.

The shading plate member 32a lying on the side of light source 22 is provided with a pair of side shading plate members 32e, 32f arranges in the width direction Y perpendicular to the carrying direction X of the carrier line 12. The spacing between the side shading plate members 32e, 32f is of the same dimension as that of the open width of each of the above slits 34a to 34d.

Lateral sides 32g, 32h, lying on the side of vegetables and fruits 16, of the side shading plate members 32e, 32f are formed so as to have contours 33e, 33f along the outline of vegetables and fruits 16. These lateral sides 32g, 32h are provided with a plurality of cuts 35a, 35b so as to facilitate the move of vegetables and fruits 16 when the vegetables and fruits 16 are carried on the carrier line 12 in the carrying direction X.

When this construction is effected, the side shading plate members 32e, 32f can shade reflected lights from neighboring vegetables and fruits 16. Further, the side shading plate members 32e, 32f define an irradiation path of measuring lights from the light sources 22a to 22c. Thus, lights other than the lights transmitted through the vegetables and fruits 16 can be efficiently shaded. Thus, the accuracy of measuring evaluation can be further enhanced and an accurate measuring evaluation can be realized.

Figure 9:
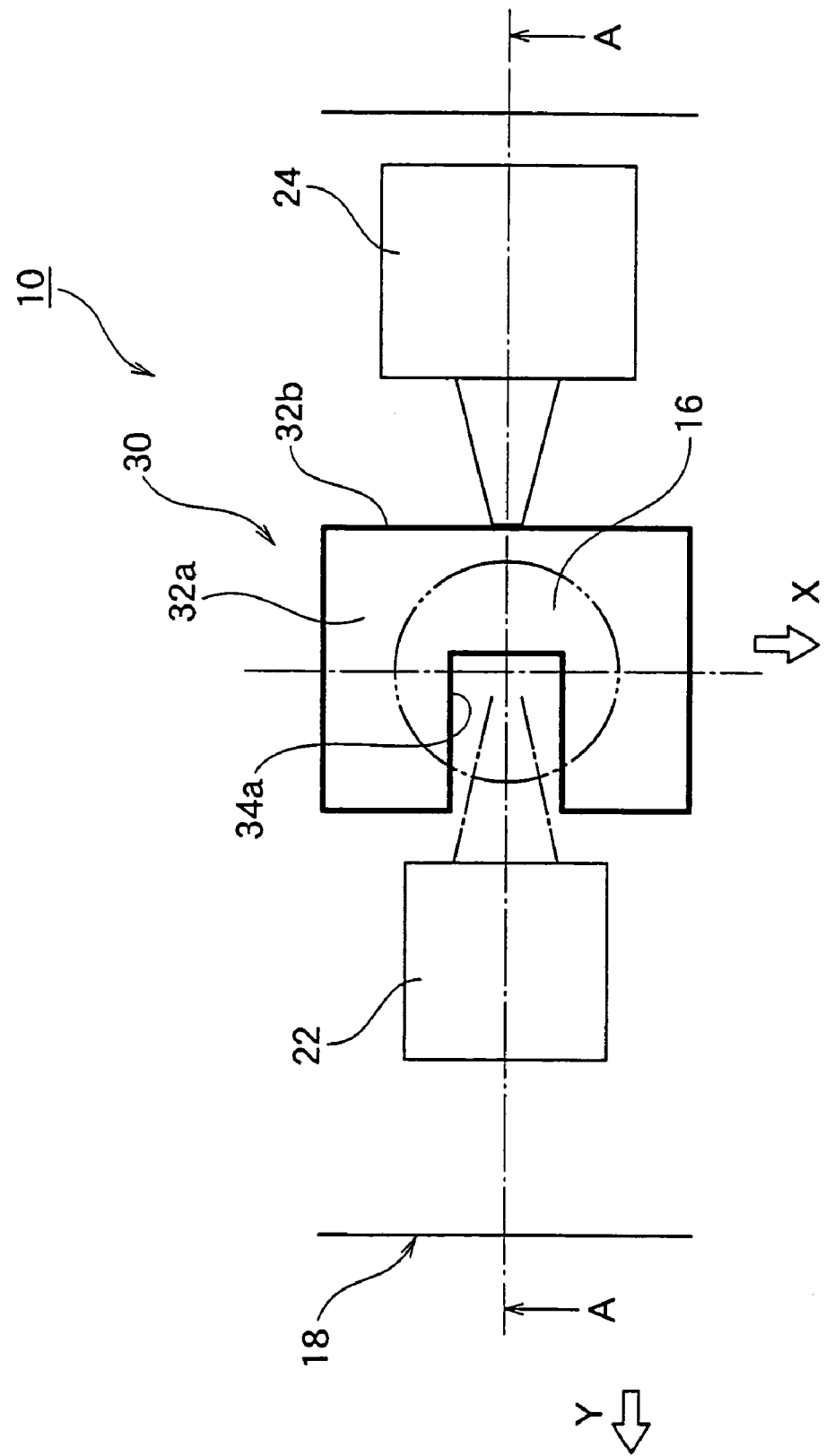
FIG. 9 is a top view of the fourth form of evaluation apparatus for vegetables and fruits according to the present invention.
Figure 10:
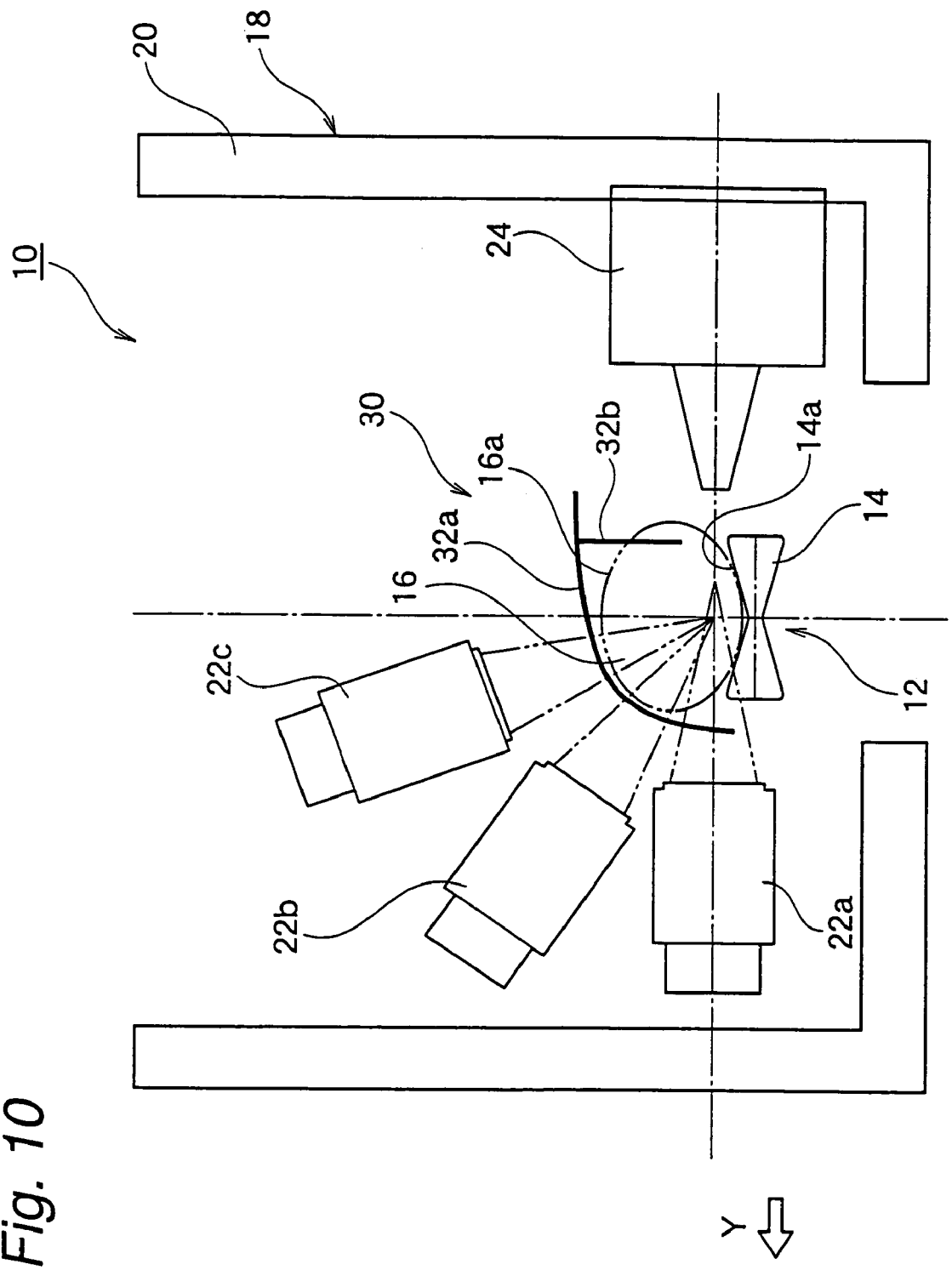
FIG. 10 is a view of section line A-A of FIG. 9.
Figure 11:
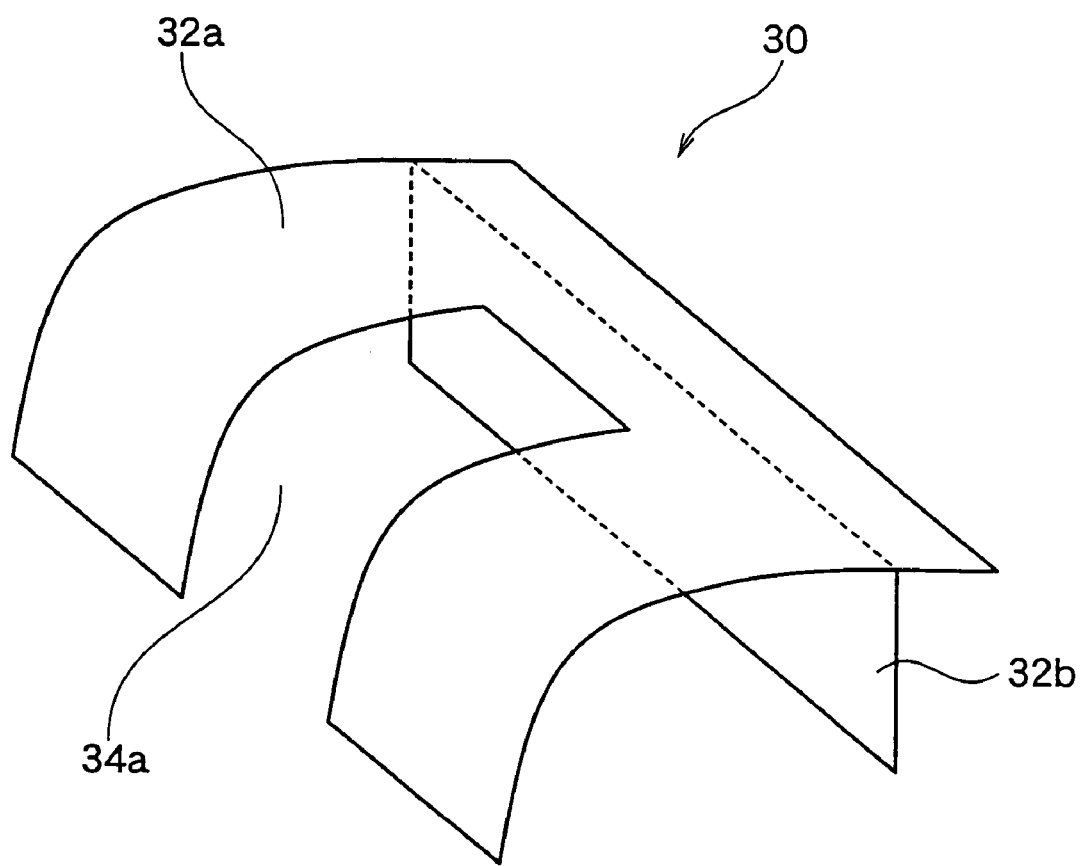
FIG. 11 is an enlarged perspective view of a shading plate.

FIG. 9 is a top view of the fourth form of evaluation apparatus for vegetables and fruits according to the present invention. FIG. 10 is a view of section line A-A of FIG. 9. FIG. 11 is an enlarged perspective view of a shading plate.

The construction of this form of evaluation apparatus 10 is fundamentally the same as that of the second form of evaluation apparatus 10 shown in FIGS. 3 to 5. Like reference numerals are used for like constituent members, and detailed description thereof will be omitted.

In this form of evaluation apparatus 10, the shading plate 30 includes shading plate member 32b arranged in parallel with the carrying direction X of the carrier line 12 on the side of light-receiving section 24.

As shown in FIGS. 10 and 11, the shading plate member 32b is provided with upper shading plate member 32a of curved surface (arcing surface) configuration which slopes from an upper end of the shading plate member 32b toward the side of light source 22 along the upper outline 16a of vegetables and fruits 16. This upper shading plate member 32a is provided with slit 34a. From the viewpoint of maintaining the curved surface configuration, it is appropriate to form the upper shading plate member 32a from a material harder than that of the shading plate member 32b.

In this construction, the shading plate members 32a, 32b effectively shade lights from the periphery of vegetables and fruits 16 other than the intended transmitted lights through vegetables and fruits 16, such as straight lights from the light sources 22a to 22c, reflected lights from vegetables and fruits 16 and reflected lights from neighboring vegetables and fruits 16.

Consequently, light-receiving section 24 does not receive any lights other than the intended transmitted lights through vegetables and fruits 16, so that the accuracy of measuring evaluation can be further enhanced and an accurate measuring evaluation can be realized.

Moreover, a tunnellike passage route for vegetables and fruits 16 along the outline of vegetables and fruits 16 is formed in the carrying direction X of the carrier line 12 by the shading plate member 32b and the upper shading plate member 32a of curved surface configuration sloping along the upper outline 16a of vegetables and fruits 16. Thus, damaging of the vegetables and fruits 16 carried on the carrier line 12 by the shading plate members 32a, 32b can be avoided. Further, the shading plate members 32a, 32b have no influence upon the position and posture of vegetables and fruits 16 on the carrier line 12, so that the accuracy of measuring evaluation can be enhanced and an accurate measuring evaluation can be realized.

Furthermore, because the shading plate members 32a, 32b are provided with the slit 34a for permitting transmission of measuring lights from the light source 22 through vegetables and fruits 16, any measuring lights from the light sources 22a to 22c are not shaded by the upper shading plate member 32a. In the virtue of the slit 34a of the upper shading plate member 32a, exposure of the vegetables and fruits 16 to measuring lights can be ensured and the measuring light is transmitted through the vegetables and fruits 16 and the transmitted measuring light can be efficiently received by the light-receiving section 24. Thus, the accuracy of measuring evaluation can be further enhanced and an accurate measuring evaluation can be realized.

Figure 12:
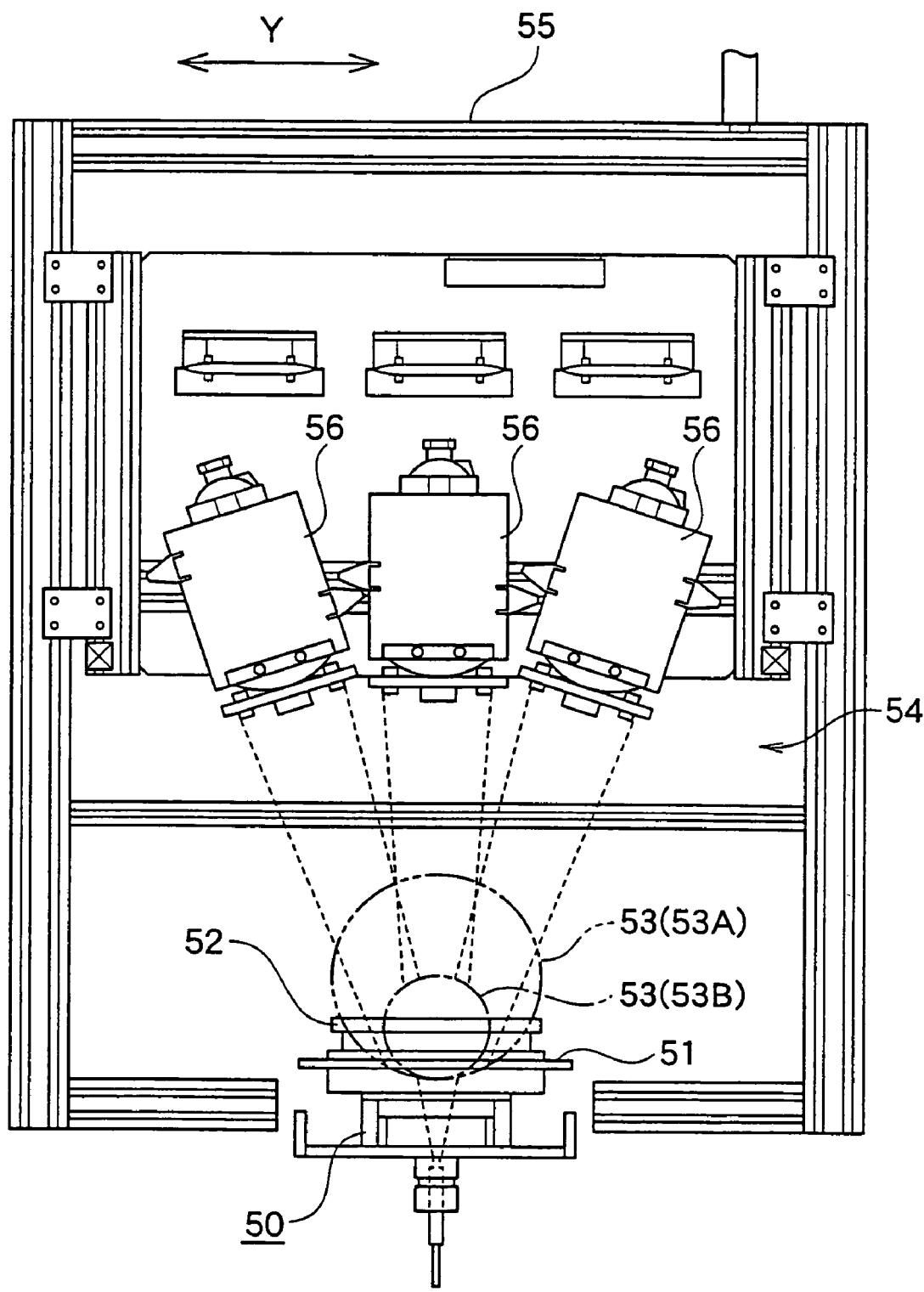
FIG. 12 is a front view of the fifth form of evaluation apparatus for vegetables and fruits according to the present invention.
Figure 13:
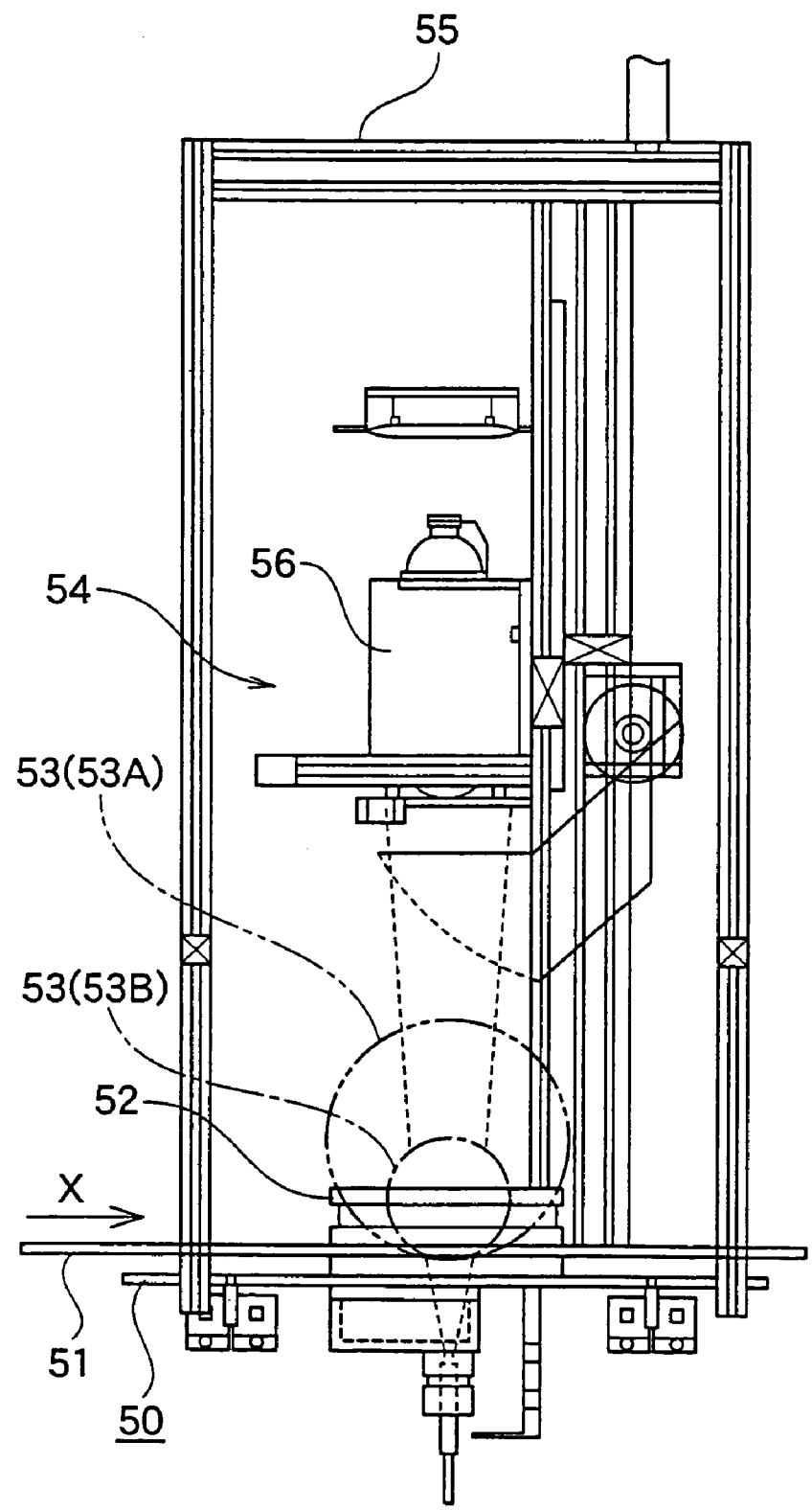
FIG. 13 is a side view of the evaluation apparatus for vegetables and fruits shown in FIG. 12.
Figure 14:
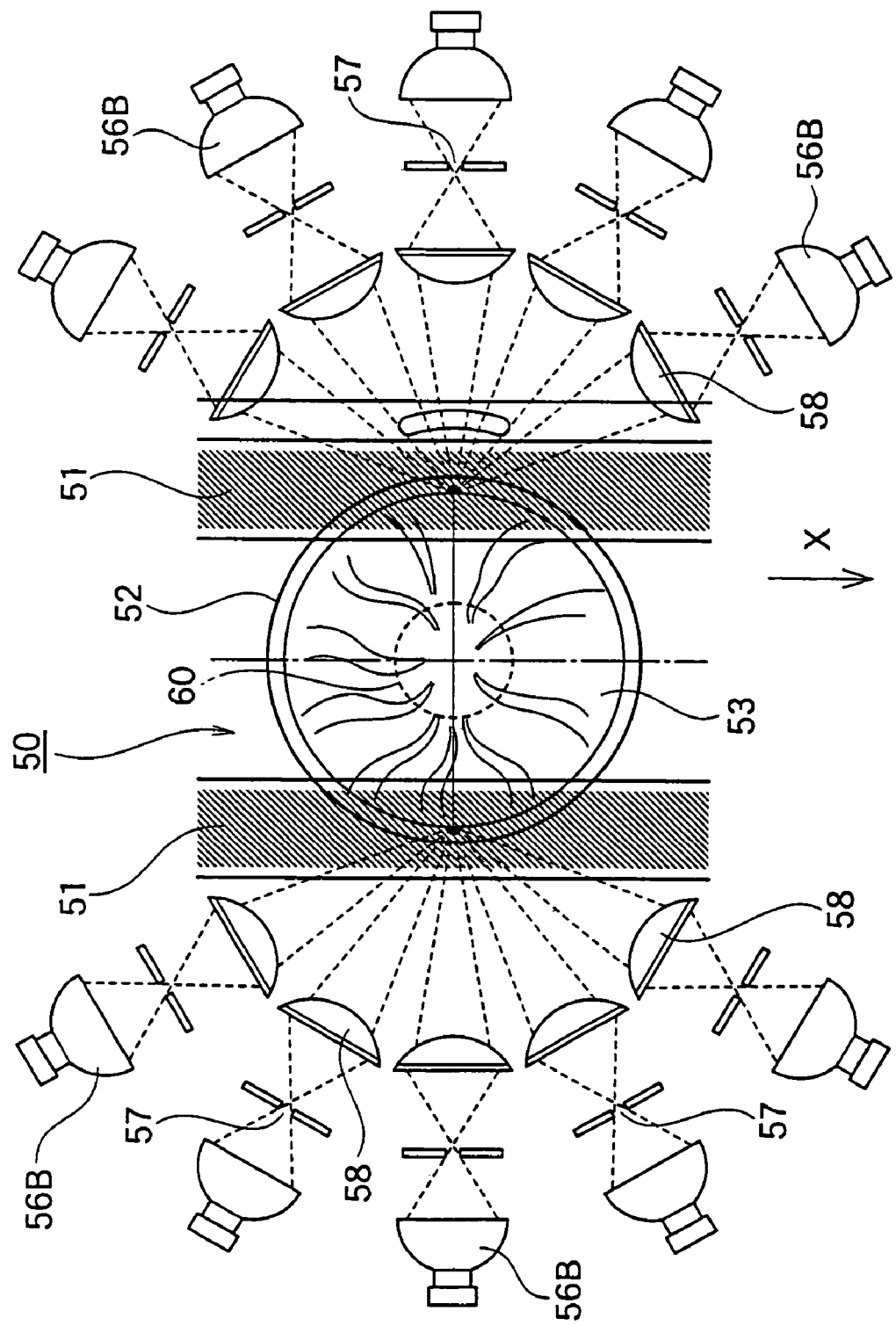
FIG. 14 is a plan view showing the arrangement of side light sources.
Figure 15:
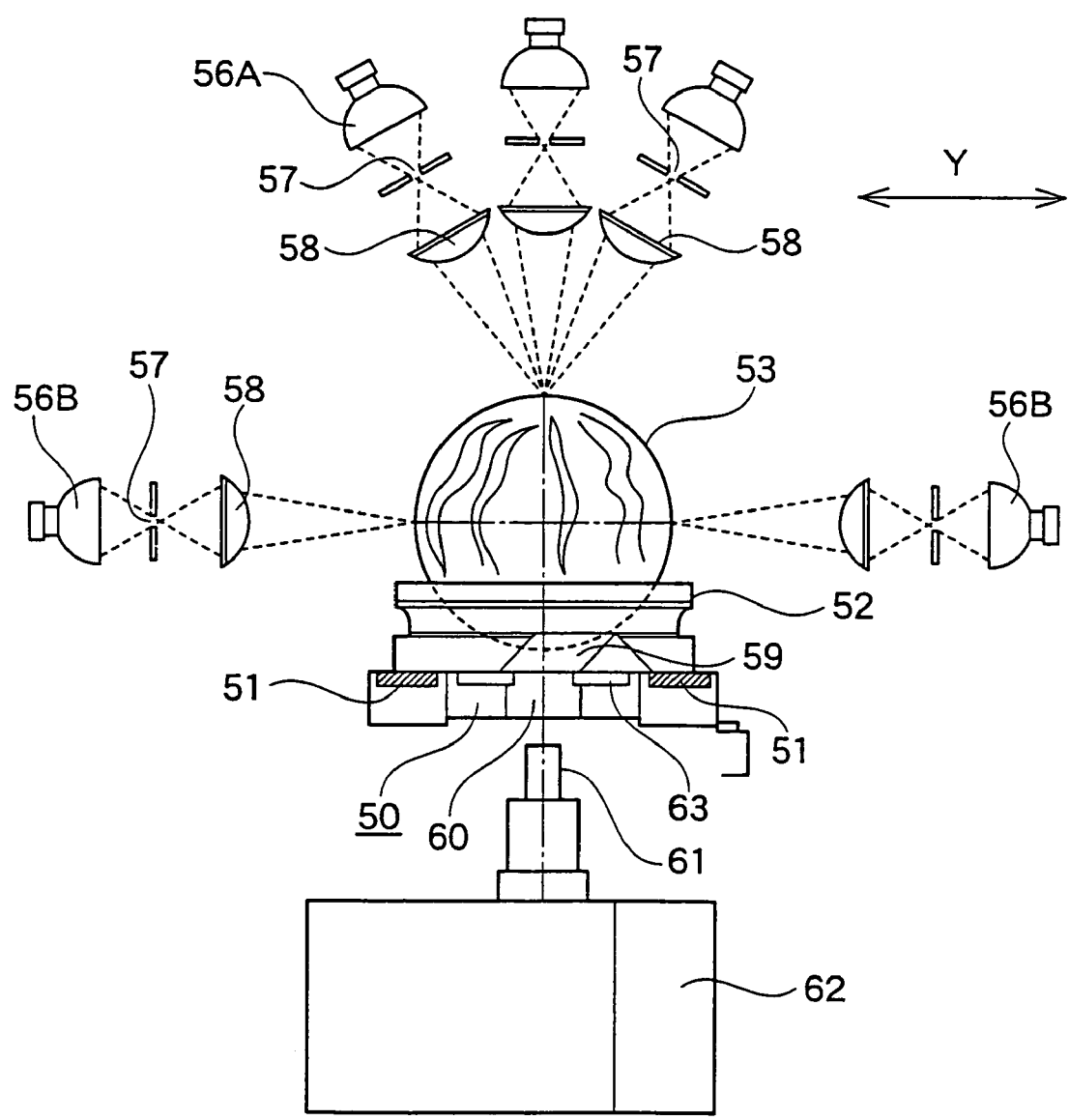
FIG. 15 is a front view showing the arrangement of upper light sources and side light sources.

FIG. 12 is a front view of the fifth form of evaluation apparatus for vegetables and fruits according to the present invention. FIG. 13 is a side view of the evaluation apparatus for vegetables and fruits shown in FIG. 12. FIG. 14 is a plan view showing the arrangement of side light sources. FIG. 15 is a front view showing the arrangement of upper light sources and side light sources.

As shown in FIGS. 12 to 15, this fifth form of evaluation apparatus for vegetables and fruits is an evaluation apparatus of such a type that, as described below, upper light sources are arranged over vegetables and fruits and side light sources are arranged along the side periphery of vegetables and fruits. In addition, in this evaluation apparatus, a light-receiving section is disposed under a carrier line and arranged to receive lights through a light-receiving window so that a measuring evaluation of vegetables and fruits can be accomplished.

In FIGS. 12 to 14, numeral 50 denotes a carrier line. Numeral 51 denotes a conveyor belt of the carrier line 50. Numeral 52 denotes a plurality of carrier trays mounted on the conveyor belt 51. The carrier trays 52 are longitudinally arranged with given spacings in the direction of length of conveyor belt 51. Numeral 53 denotes vegetables and fruits placed on the carrier trays 52. Numeral 53A denotes vegetables and fruits of large size, while numeral 53B denotes vegetables and fruits of small size.

Numeral 54 denotes an evaluation apparatus installed at an appropriate site along the carrier line 50. Numeral 55 denotes a frame of the evaluation apparatus 54. The frame 55 is provided with a plurality of light sources 56 for new infrared radiation. The light sources 56 are arranged in such a construction that, when vegetables and fruits 53 carried on the carrier trays 52 pass a given measuring point, the vegetables and fruits 53 can be evenly exposed to lights therefrom.

In this form of evaluation apparatus, a plurality of upper light sources 56A for irradiating measuring lights from overhead toward the vegetables and fruits 53 are arranged in a row in horizontal direction (width direction) Y perpendicular to the carrying direction X of the conveyor belt 51. Further, a plurality of side light sources 56B for irradiating measuring lights from right and left sides toward the vegetables and fruits 53 are arranged in dispersion on the circumference of a circle centering on the measuring point.

The measuring lights irradiated from the vast plurality of light sources 56 arranged in the above construction are passed through irradiation slit 57 and condenser lens 58 so as to converge on the center of vegetables and fruits 53. In the irradiation of measuring lights, quantities of the light are regulated in accordance with the size of vegetables and fruits 53.

Figure 20:
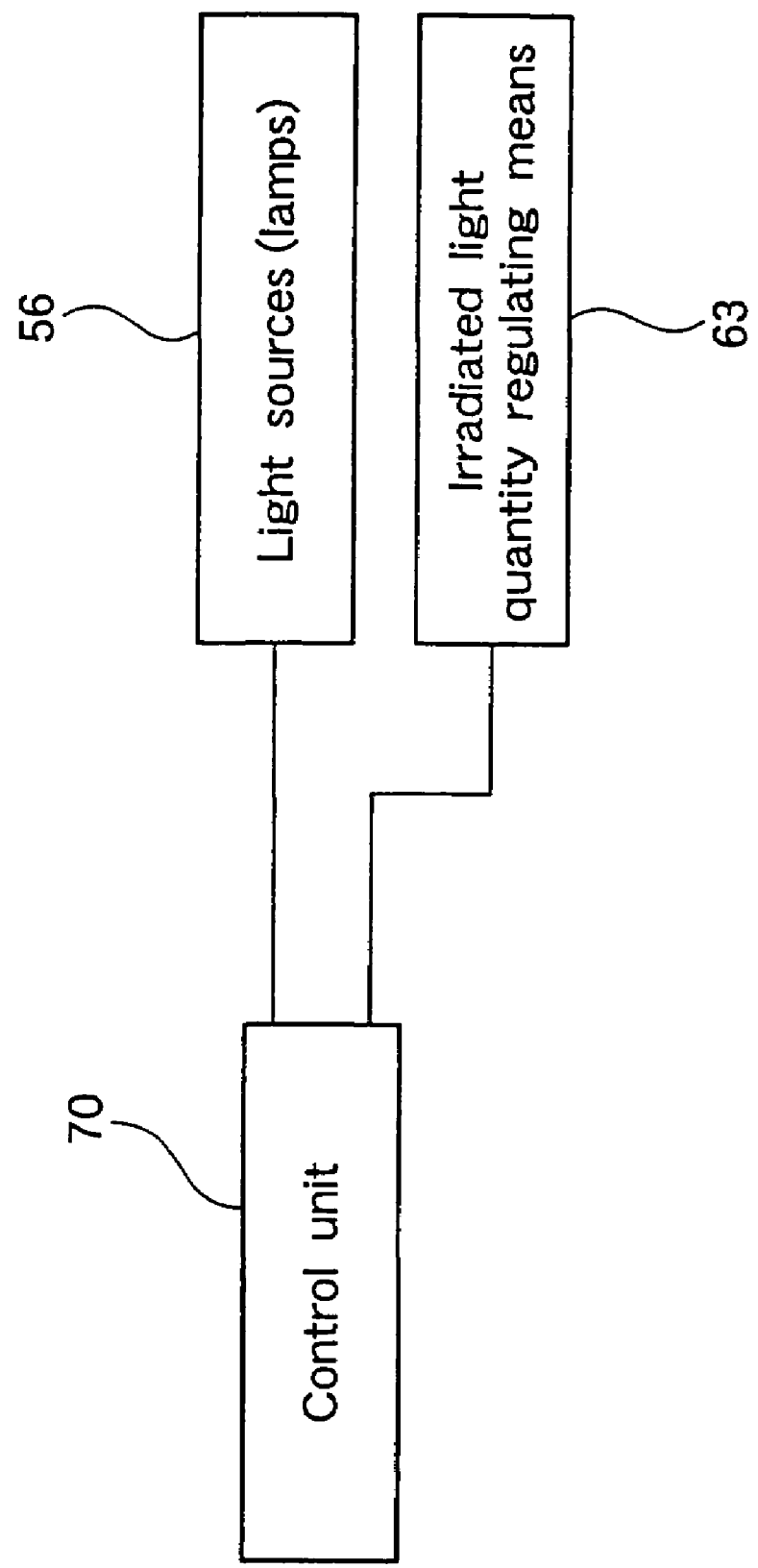
FIG. 20 is a block circuit diagram.
Figure 22:
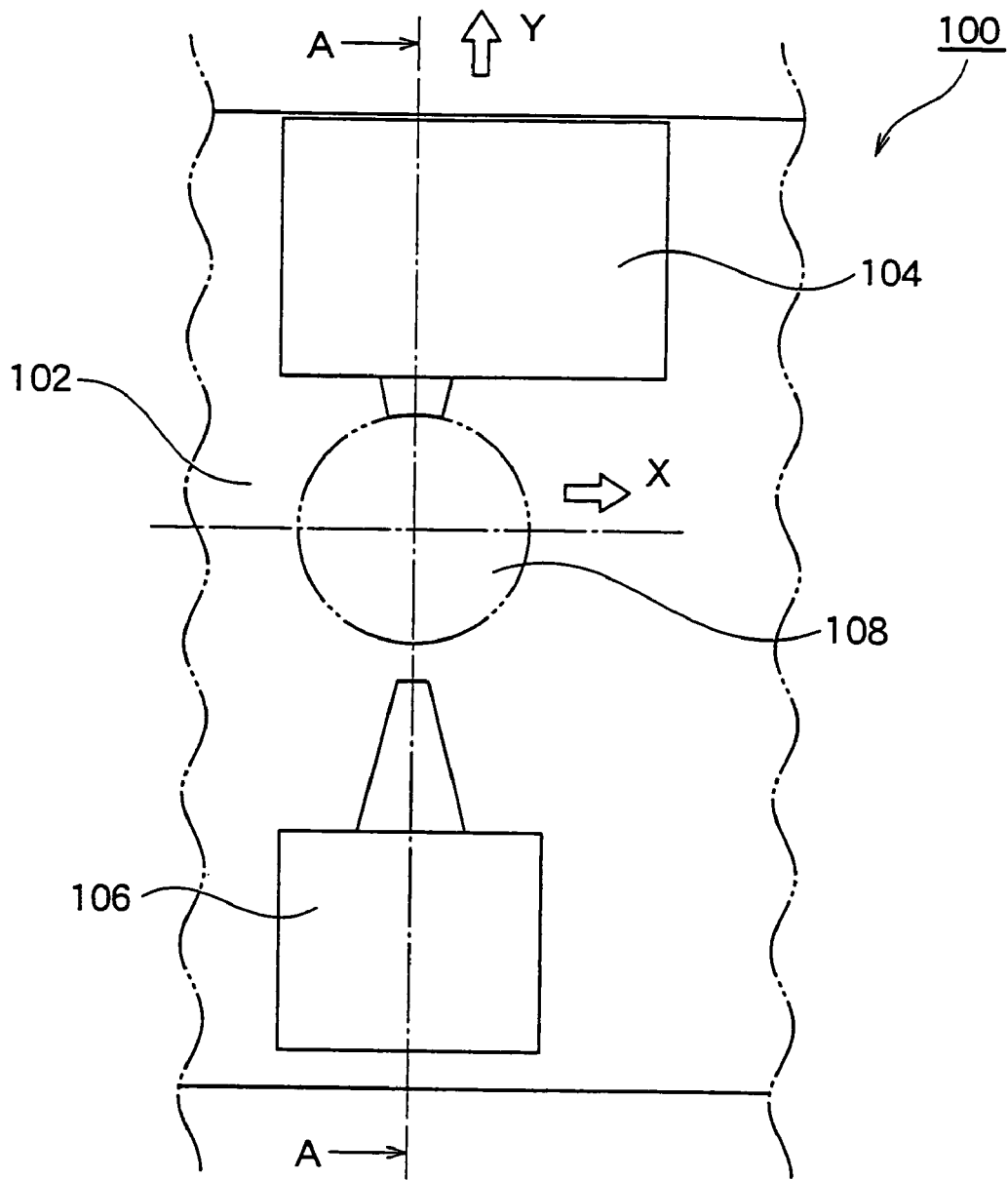
FIG. 22 is a top view of the conventional evaluation apparatus of single transmitted light type for vegetables and fruits.
Figure 23:
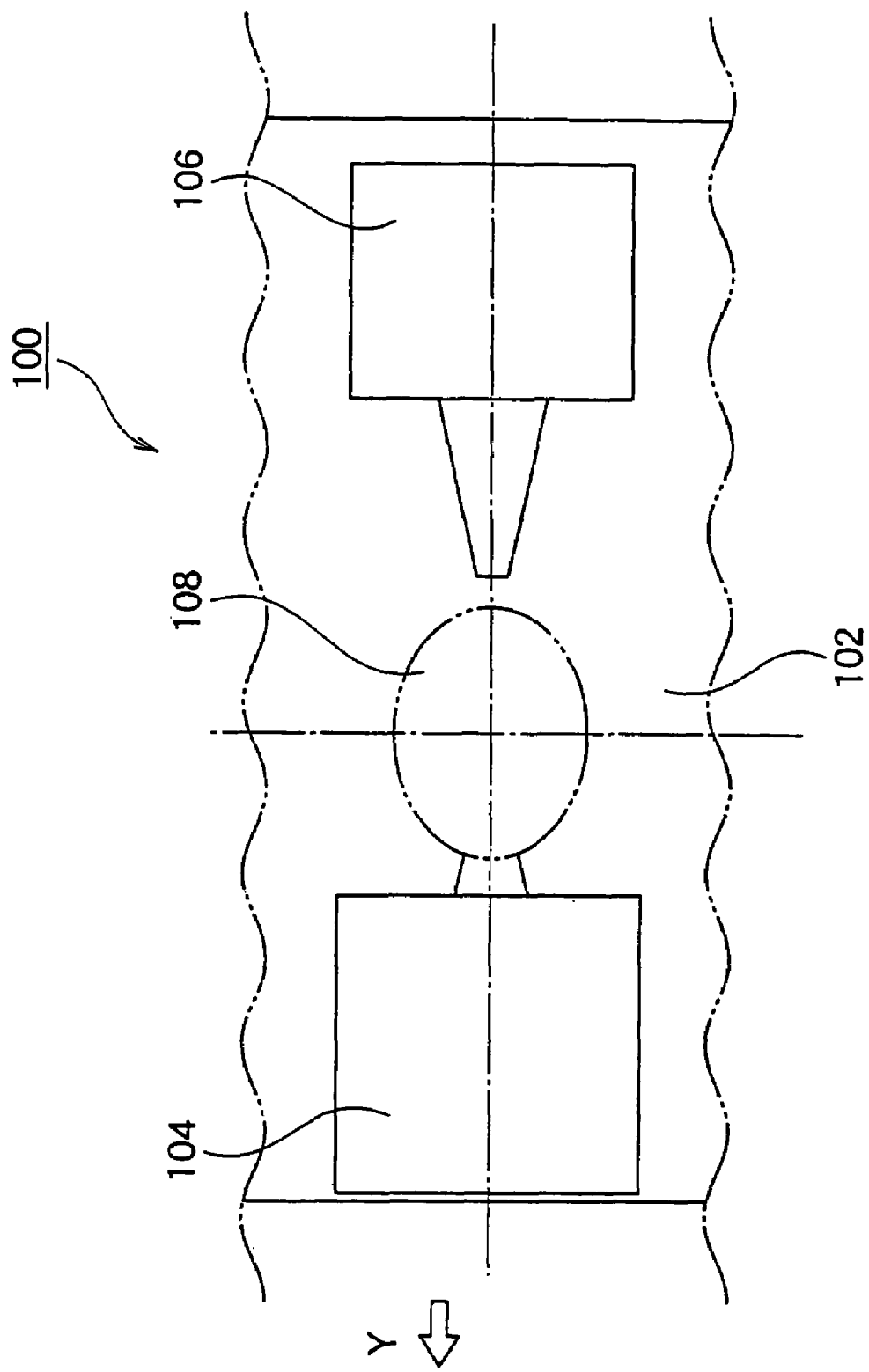
FIG. 23 is a view of section line A-A of FIG. 22.
Figure 24:
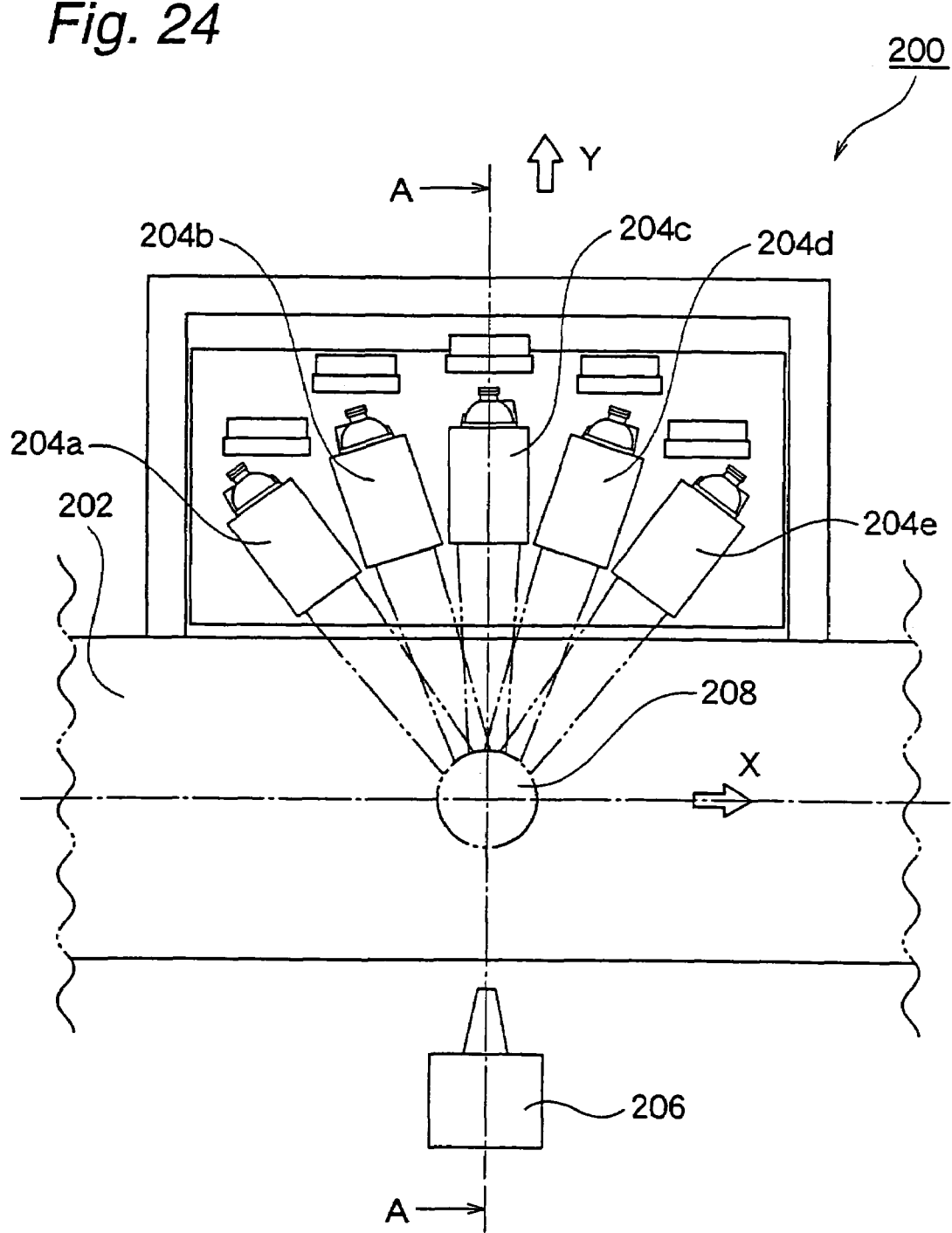
FIG. 24 is a top view of the conventional evaluation apparatus of transmitted light type for vegetables and fruits.
Figure 25:
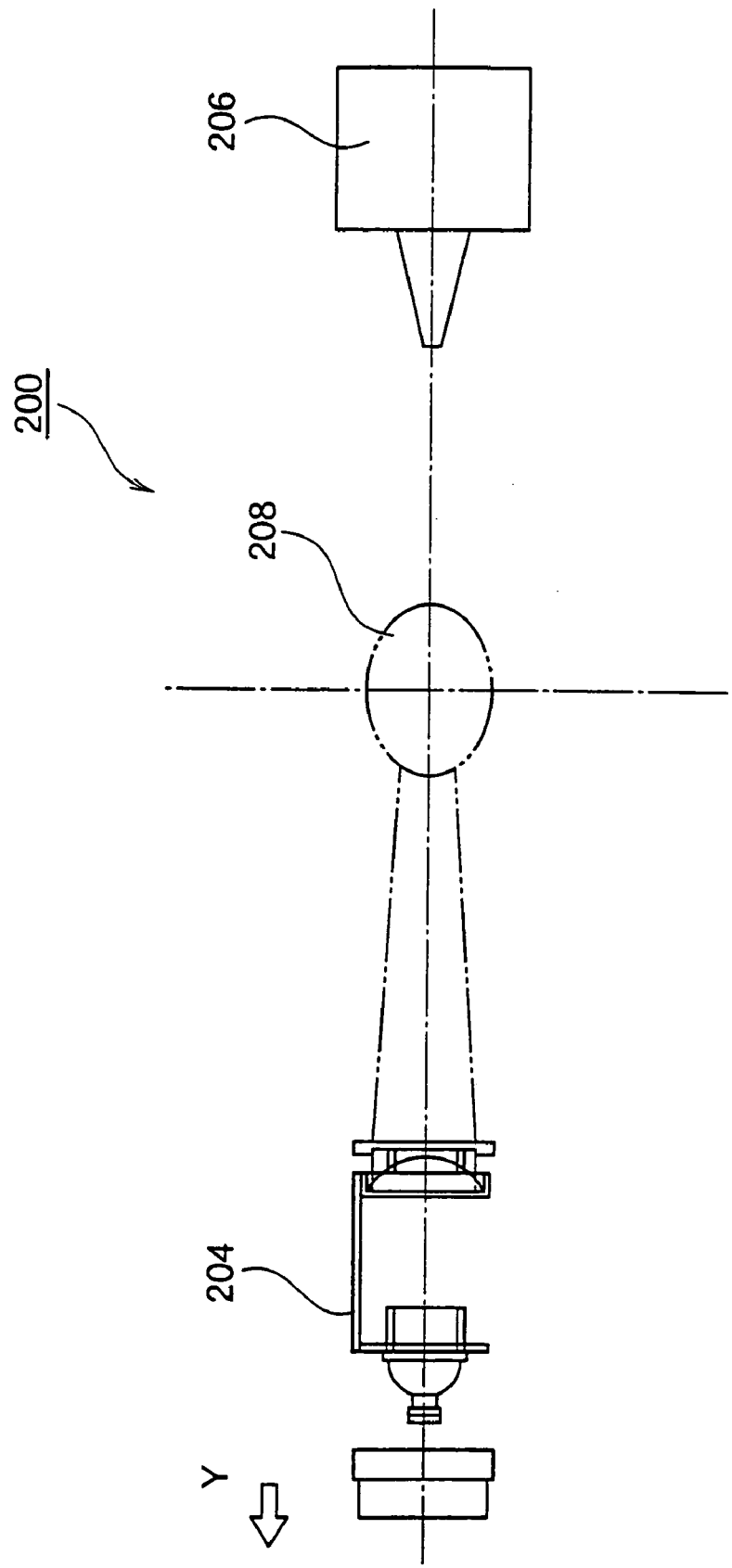
FIG. 25 is a view of section line A-A of FIG. 24.

Specifically, in this form of evaluation apparatus, the regulation of quantities of irradiated light can be accomplished by changing the number of lit light sources 56 in accordance with the size of vegetables and fruits 53 as specified in the table of FIG. 21 by the use of control unit 70 (FIG. 20).

Further, in the regulation of the number of lit light sources, lighting of the light sources 56 may be performed in such a manner that, for example, every second one or every third one is lit so as to enable exposure of the vegetables and fruits 53 to measuring lights at varied angles. Also, the angles of light sources 56 may be changed in accordance with the size of vegetables and fruits 53 to thereby enable converging of measuring lights on the center of each of vegetables and fruits 53. With respect to the side light sources 56B, they may be slid up and down.

Each of the carrier trays 52 at the bottom is provided with up-and-down transmission hole 59 (FIG. 15). The measuring lights irradiated from the light sources 56 toward vegetables and fruits 53 are transmitted through the interior of vegetables and fruits 53 and emitted through the transmission hole 59 of carrier trays 52.

Numeral 60 denotes a light-receiving window provided in the carrier line 50. Numeral 61 denotes a light-receiving section disposed under the light-receiving window 60. When each carrier tray 52 reaches a given measuring point, the transmission hole 59 of the carrier tray 52 vertically lies on the light-receiving window 60, so that the transmitted lights having passed through the transmission hole 59 are led into the light-receiving section 61. The transmitted lights having been received by the light-receiving section 61 are analyzed by analyzer 62, so that measuring of the interior quality (sweetness degree, acidity, maturity grade, etc.) of vegetables and fruits 53 can be accomplished.

Figure 16:
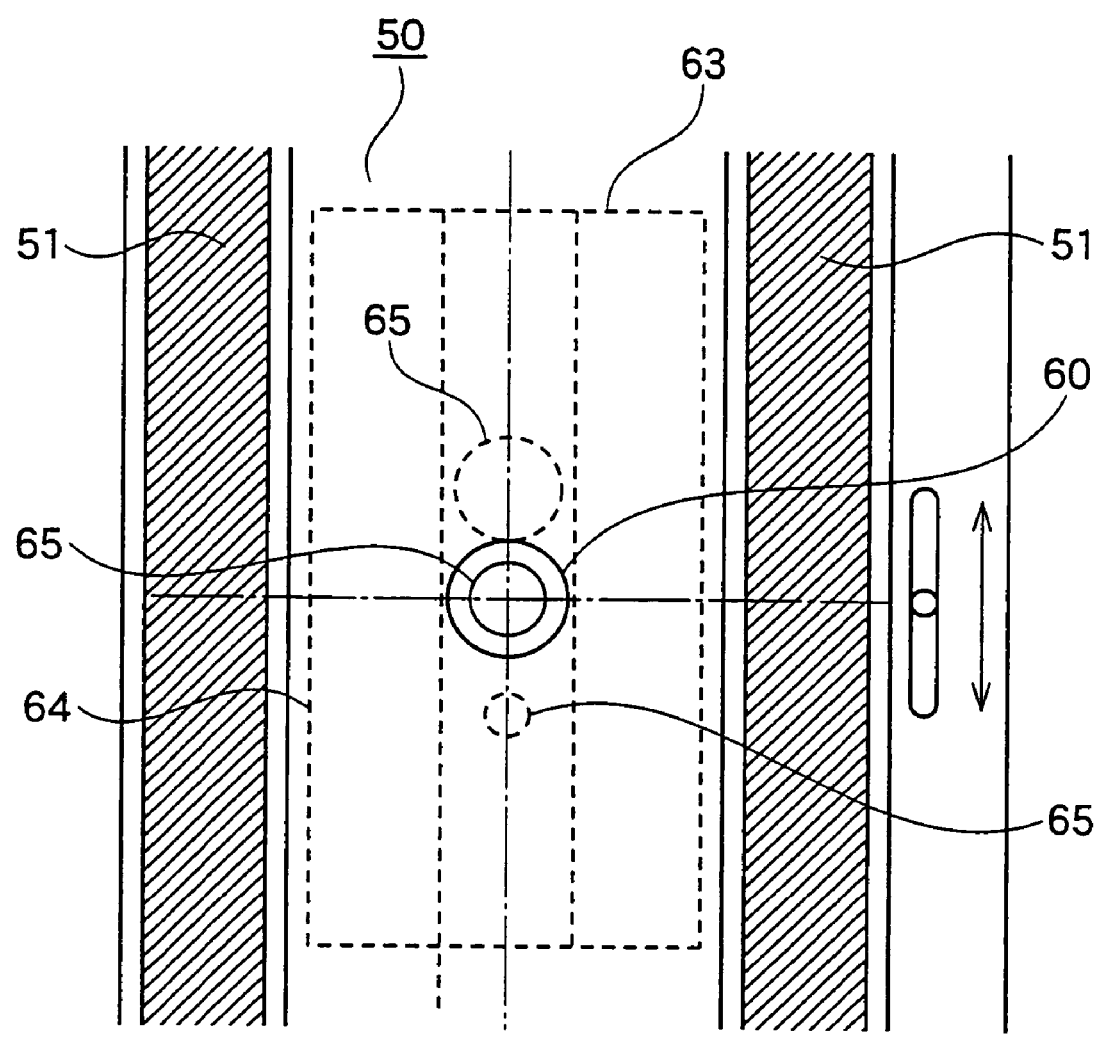
FIG. 16 is a plan showing the mechanism of regulation of quantity of transmitted light with the use of a slide plate.
Figure 17:
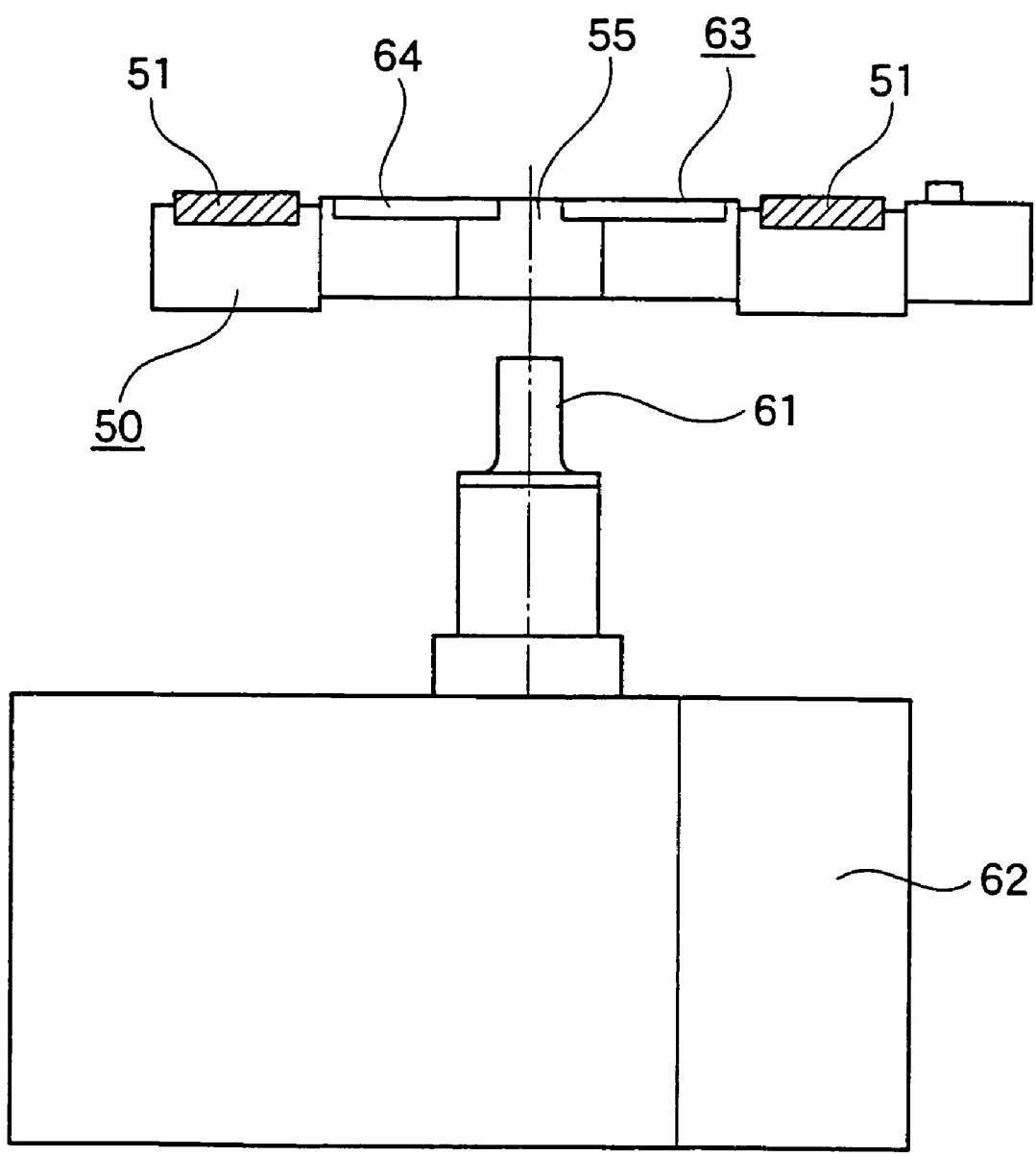
FIG. 17 is a front view of the showing of FIG. 16.

Numeral 63 denotes transmitted light quantity regulating means provided in the carrier line 50. As shown in FIGS. 16 and 17, the transmitted light quantity regulating means 63 includes slide plate 64 slidably secured to the carrier line 50 and a plurality of apertures 65 of different diameters provided in the slide plate 64.

Figure 18:
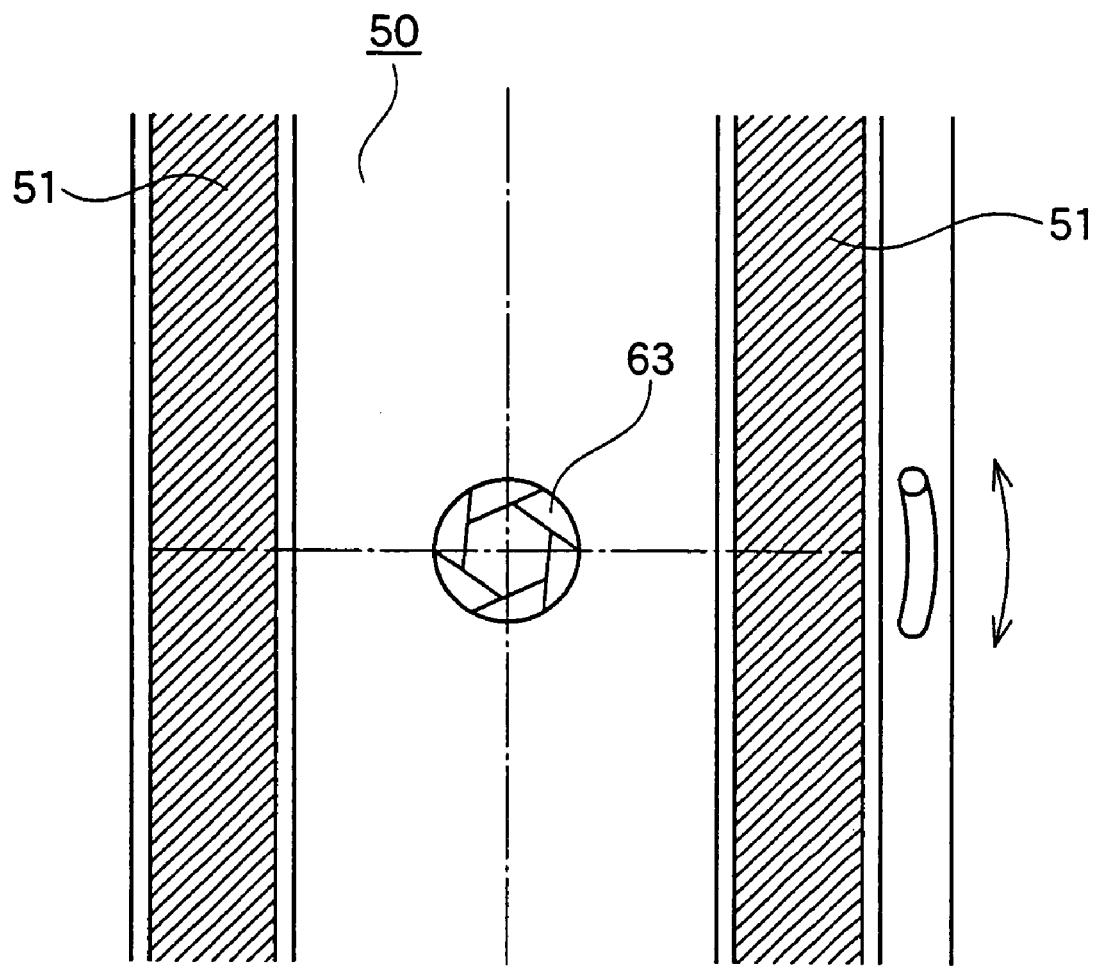
FIG. 18 is a plan view showing the mechanism of regulation of quantity of transmitted light with the use of a camera aperture.
Figure 19:
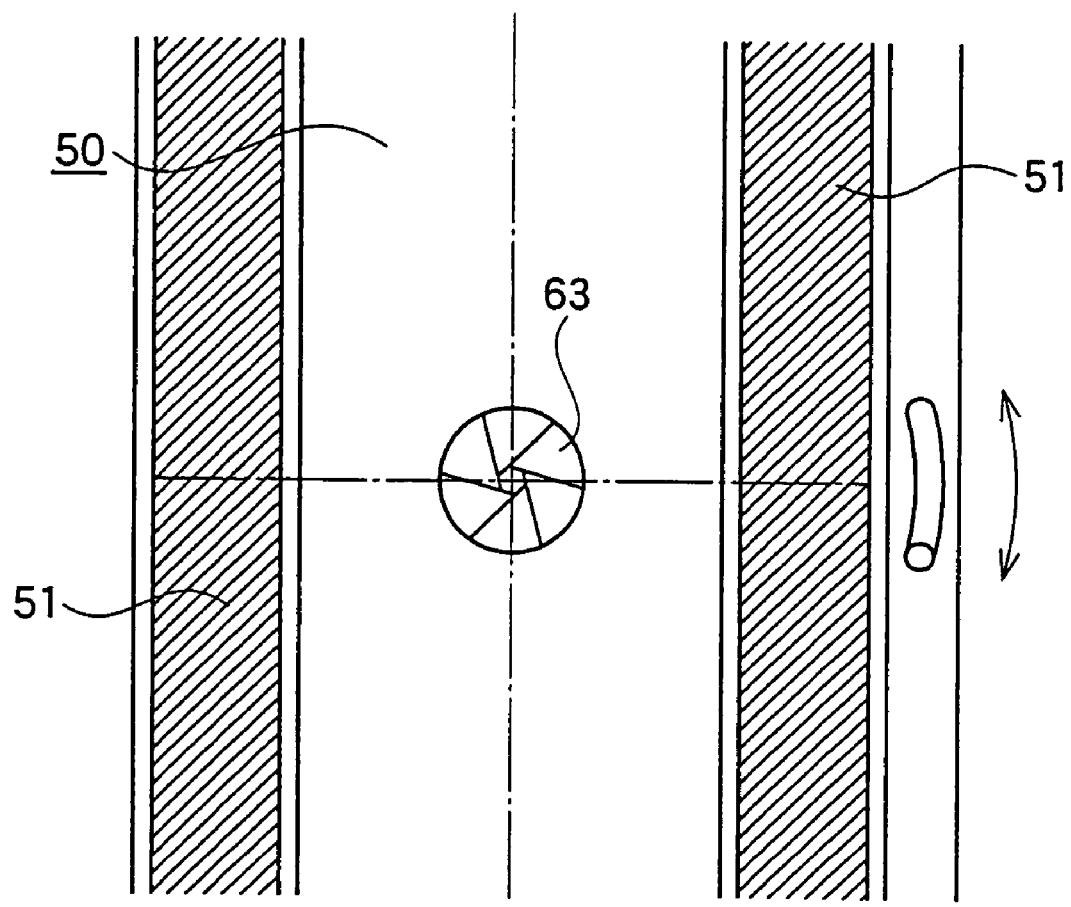
FIG. 19 is a plan view showing the mechanism of regulation of quantity of transmitted light with the use of a camera aperture.

Sliding of the slide plate 64 so as to bring aperture 65 of desired size upon the light-receiving window 60 enables regulating the openness of light-receiving window 60, thereby accomplishing regulation of quantities of transmitted light. The transmitted light quantity regulating means 63, as shown in FIGS. 18 and 19, may have the same mechanism as that of a camera aperture.

In the evaluation apparatus for vegetables and fruits constructed in the above manner, a combination pattern as indicated in the table of FIG. 21 is registered in the control unit 70 in advance. For example, for watermelons of large size among the vegetables and fruits 53, large quantities of irradiated light are required, so that 10 light sources 56 are lit. Thus, quantities of transmitted light to be received must also be large, so that the light-receiving window 60 is set for large openness. On the other hand, for tangerines of small size, three light sources 56 are lit, and the light-receiving window 60 is set for small openness.

In the carrying measurement of watermelons, the item "watermelon" is selected, and the slide plate 64 is slid so as to set the light-receiving window 60 for large openness, thereby initiating the measuring operation. Although the sliding of the slide plate 64 is performed manually, it is preferred to automatically perform the sliding by a motor power under the control of the control unit 70 in accordance with the item set.

When each carrier tray 52 on which a watermelon is placed reaches a given measuring point, 10 light sources 56 are lit as indicated in the table of FIG. 21, so that the watermelon on the carrier tray 52 is evenly exposed to measuring lights irradiated at varied angles. Then, measuring lights are transmitted through the interior of watermelon. Transmitted lights are led through the transmission hole 59 of the carrier tray 52 and further through the light-receiving window 60 and received by the light-receiving section 61. The received lights are analyzed by the analyzer 62, thereby accomplishing measuring evaluation of the interior quality (sweetness degree, acidity, maturity grade, etc.) of the watermelon.

When it is intended to conduct the carrying measurement of tangerines after the carrying measurement of watermelons, selection of the item "tangerine" on the control unit 70 leads to selection of three light sources 56 suitable for the measurement of tangerines, so that appropriate regulation of light quantities can be accomplished. Thus, thereafter, only setting the light-receiving window 60 for small openness by sliding the slide plate 64 is required to realize simple change of all settings from watermelons to tangerines.

The quantity of lights irradiated from the light sources 56 can be regulated by the power source resistance or shading plate applied to the light sources 56. However, when the items are frequently changed in a day, it is preferred to effect the regulation by the shading plate. The reason is that, in the regulation by the power source resistance or the number of lit light sources 56, warming up of about one hour would be needed to stabilize photospectra.

On the other hand, when the frequency of item change is low, the regulation by the number of lit light sources 56 or by the power source resistance is preferred. The reason is that the regulation by the shading plate would incur high mechanical cost.

Preferred embodiments of the present invention have been described above, to which, however, the present invention is in no way limited. For example, the arrangement and configuration of shading plate members are not limited to those of the above embodiments, and various configurations and arrangements can be employed as long as lights other than intended transmitted lights can be shaded so as to prevent incidence thereof upon the light-receiving section. Further, accordingly, various modifications and changes can be made as long as such do not depart from the object and gist of the present invention.

In the present invention, vegetables and fruits are exposed to measuring lights irradiated from a plurality of light sources vertically arranged by one side of a carrier line in the width direction Y perpendicular to the carrying direction X of the carrier line. Therefore, during the measurement of vegetables and fruits being moved on the carrier line, especially at the beginning or ending of measurement, the light-receiving section does not receive any lights from the periphery of vegetables and fruits other than the intended transmitted lights, such as straight lights vegetables and fruits. As a result, the accuracy of measuring evaluation can be strikingly enhanced and an accurate measuring evaluation can be realized.

Further, in the present invention, the plurality of vertically arranged light sources are preferably disposed so that an angle α from the width direction Y perpendicular to the carrying direction X of the carrier line is in the range of 90° or less. Consequently, only lights having been transmitted through the vegetables and fruits are received by the light-receiving section. Therefore, receiving of reflected lights from the vegetables and fruits, etc. by the light-receiving section can be avoided, so that the accuracy of measuring evaluation can be further enhanced and an accurate measuring evaluation can be realized.

Also, in the present invention, a shading plate preferably arranged between the light sources and the light-receiving section shade any lights from the periphery of vegetables and fruits other than the intended lights having been transmitted through vegetables and fruits, such as straight lights from the light sources, reflected lights from vegetables and fruits and reflected lights from neighboring vegetables and fruits. Therefore, the light-receiving section does not receive any lights other than the intended lights having been transmitted through vegetables and fruits. Therefore, the accuracy of measuring evaluation can be further enhanced and an accurate measuring evaluation can be realized.

Still further, in the present invention, a tunnellike passage route for vegetables and fruits along the outline of vegetables and fruits is formed in the carrying direction X of the carrier line. Thus, damaging of the vegetables and fruits carried on the carrier line by shading plate members can be avoided. Furthermore, the shading plate members have no influence upon the position and posture of vegetables and fruits on the carrier line, so that the accuracy of measuring evaluation can be enhanced and an accurate measuring evaluation can be realized. Also, the light-receiving member does not receive any lights from the periphery of vegetables and fruits other than the intended transmitted lights through vegetables and fruits, such as straight lights from the light sources, reflected lights from vegetables and fruits and reflected lights from neighboring vegetables and fruits, through any gap between the lower end portions of shading plate members and the vegetables and fruits. As a result, the accuracy of measuring evaluation can be further enhanced and an accurate measuring evaluation can be realized.

Moreover, in the present invention, side shading plate members can be shade reflected lights from neighboring vegetables and fruits. Further, the side shading plate members define an irradiation path of measuring lights from the light sources. Thus, lights other than the lights having been transmitted through the vegetables and fruits can be efficiently shaded, so that the accuracy of measuring evaluation can be further enhanced and an accurate measuring evaluation can be realized.

In the present invention, measuring lights irradiated from the light sources can pass through slits provided in the shading plate to vegetables and fruits without being shaded by the shading plate members, and the lights having been transmitted through the vegetables and fruits can be efficiently received by the light-receiving section. Thus, the accuracy of measuring evaluation can be enhanced, and an accurate measuring evaluation can be realized.

Further, in the present invention, the shading plate is preferably so constructed as to be vertically movable in accordance with the size of vegetables and fruits. Even when the size of vegetables and fruits is varied, lights other than the lights having been transmitted through the vegetables and fruits can be efficiently shaded by the shading plate, so that the accuracy of measuring evaluation can be enhanced and an accurate measuring evaluation can be realized.

Moreover, in the present invention, the quantity of measuring lights from the light sources can be regulated by the plurality of arranged light sources in accordance with the size of vegetables and fruits and the quantity of transmitted lights received by the light-receiving section can be regulated by regulating the openness of light-receiving window with the use of the regulating means for quantity of transmitted light. Thus, the quantity of measuring lights and the quantity of transmitted lights can be regulated appropriately and simply in accordance with the size of vegetables and fruits. Therefore, the evaluation of vegetables and fruits of varied item species and sizes can be accomplished on a single carrier line with economic advantage.

Also, the present invention can be so constituted as to enable regulating the quantity of measuring lights from light sources by controlling the number of lit light sources. Thus, the quantity of measuring lights can be regulated without changing the intensity of individual light sources (lamps), so that the regulation of lights transmitted through vegetables and fruits can be appropriately performed.

Further, in the present invention, the interior quality of vegetables and fruits can be measured with high accuracy by causing upper light sources and side light sources to irradiate measuring lights from overhead and right and left sides, respectively, toward the vegetables and fruits.

Still further, in the present invention, the interior quality of vegetables and fruits can be measured with high accuracy by evenly exposing the vegetables and fruits to measuring lights irradiated from overhead by a plurality of upper light sources arranged in a row in the right and left direction Y perpendicular to the carrying direction X of the carrier line.

Still further, in the present invention, the interior quality of vegetables and fruits can be measured with high accuracy by evenly exposing the vegetables and fruits to measuring lights-irradiated from lateral sides by side light sources arranged in dispersion on the circumference of a circle. As is apparent from the above, the present invention highly advantageously exerts a variety of striking and characteristic functions and effects.

What is claimed is:

1. An evaluation apparatus for vegetables and fruits capable of evaluating vegetables and fruits with respect to their interior quality through exposing vegetables and fruits carried on a carrier line, which evaluation apparatus comprises:
a plurality of light sources vertically arranged exclusively in a common plane on one side of a carrier line spaced in a width direction Y from the carrier line and wherein the common plane of the light sources is perpendicular to a carrying direction X of the carrier line; and
a light-receiving section arranged by an opposite side of the carrier line in the width direction Y perpendicular to the carrying direction X of the carrier line and arranged exclusively in the common plane of the light sources; and wherein
measuring lights irradiated from the light sources converge toward the vegetables and fruits whereby the measuring lights are transmitted through the vegetables and fruits so that the light-receiving section receives the transmitted measuring light.

2. The evaluation apparatus for vegetables and fruits as claimed in claim 1, wherein the plurality of vertically arranged light sources are each disposed at an angle from the width direction Y perpendicular to the carrying direction X of the carrier line, said angle in the range of not more than 90°.

3. The evaluation apparatus for vegetables and fruits as claimed in claim 1, which further comprises a shading plate interposed between the light sources and the light-receiving section, the shading plate being capable of shading lights other than the measuring lights transmitted through vegetables and fruits so as to avoid receiving of lights other than the measuring lights having been transmitted through vegetables and fruits by the light-receiving section.

4. The evaluation apparatus for vegetables and fruits as claimed in claim 3, wherein the shading plate comprises shading plate members disposed in parallel with the carrying direction X of the carrier line.

5. The evaluation apparatus for vegetables and fruits as claimed in claim 3, wherein the shading plate comprises a plurality of shading plate members disposed in parallel with the carrying direction X of the carrier line, the plurality of shading plate members being arranged in parallel relationship with given spacings in the width direction Y of the carrier line.

6. The evaluation apparatus for vegetables and fruits as claimed in claim 5, wherein the plurality of shading plate members arranged in parallel relationship with given spacings in the width direction Y of the carrier line have lengths which are those having lower end portions along an outline of vegetables and fruits.

7. The evaluation apparatus for vegetables and fruits as claimed in claim 3, wherein the shading plate comprises side shading plate members arranged in the width direction Y perpendicular to the carrying direction X of the carrier line.

8. The evaluation apparatus for vegetables and fruits as claimed in claim 3, wherein the shading plate comprises an upper shading plate member of configuration along an upper outline of vegetables and fruits.

9. The evaluation apparatus for vegetables and fruits as claimed in claim 3, wherein the shading plate is provided with slits for enabling exposure of the vegetables and fruits to the measuring lights from the light sources.

10. The evaluation apparatus for vegetables and fruits as claimed in claim 3, wherein the shading plate is so constructed to be vertically movable in accordance with sizes of vegetables and fruits.

11. The evaluation apparatus for vegetables and fruits as claimed in claim 1, wherein the plurality of vertically arranged light sources are so constructed as to permit selection of light sources for irradiating measuring lights toward vegetables and fruits in accordance with sizes and types of vegetables and fruits.

12. The evaluation apparatus for vegetables and fruits as claimed in claim 1, wherein the measuring lights converge at a center of the vegetable or fruit.

13. A method for evaluation of vegetables and fruits comprising:
exposing vegetables and fruits to measuring lights irradiated from a plurality of light sources vertically arranged exclusively in a common plane on one side of a carrier line in a width direction Y perpendicular to a carrying direction X of the carrier line wherein the measuring lights converge toward the vegetables and fruits; and
providing a light-receiving section arranged by an opposite side of the carrier line spaced in the width direction Y from the carrier line and wherein the common plane of the light sources is perpendicular to the carrying direction X of the carrier line and arranged exclusively in the common plane of the light sources to receive the measuring lights having been transmitted through the vegetables and fruits to thereby enable evaluation of the vegetables and fruits with respect to their interior quality.

14. The method for evaluation of vegetables and fruits as claimed in claim 13, wherein the plurality of vertically arranged light sources are disposed so that an angle a from the width direction Y perpendicular to the carrying direction X of the carrier line is in the range of not more than 90°.

15. The method for evaluation of vegetables and fruits as claimed in claim 13, wherein a shading plate is interposed between the light sources and the light-receiving section so as to shade lights other than the measuring lights transmitted through vegetables and fruits, thereby avoiding receiving of lights other than the measuring lights having been transmitted through vegetables and fruits by the light-receiving section.

16. The method for evaluation of vegetables and fruits as claimed in claim 15, wherein the shading plate comprises a plurality of shading plate members disposed in parallel with the carrying direction X of the carrier line, the plurality of shading plate members arranged in parallel relationship with given spacings in the width direction Y of the carrier line.

17. The method for evaluation of vegetables and fruits as claimed in claim 16, wherein the plurality of shading plate members arranged in parallel relationship with given spacings in the width direction Y of the carrier line have lengths which are those having lower end portions along an outline of vegetables and fruits.

18. The method for evaluation of vegetables and fruits as claimed in claim 15, wherein the shading plate comprises side shading plate members arranged in the width direction Y perpendicular to the carrying direction X of the carrier line.

19. The method for evaluation of vegetables and fruits as claimed in claim 15, wherein the shading plate comprises an upper shading plate member of configuration along an upper outline of vegetables and fruits.

20. The method for evaluation of vegetables and fruits as claimed in claim 15, wherein the shading plate is provided with slits for enabling exposure of the vegetables and fruits to the measuring lights from the light sources.

21. The method for evaluation of vegetables and fruits as claimed in claim 15, wherein the shading plate is so constructed to be vertically movable in accordance with sizes of vegetables and fruits.

22. The method for evaluation of vegetables and fruits as claimed in claim 13, wherein the measuring lights converge at a center of the vegetable or fruit.

* * * * *

UNITED STATES PATENT AND TRADEMARK OFFICE
CERTIFICATE OF CORRECTION

| | | |
|---|---|---|
| PATENT NO. | : 7,295,318 B2 | Page 1 of 1 |
| APPLICATION NO. | : 11/429794 | |
| DATED | : November 13, 2007 | |
| INVENTOR(S) | : Taniguchi et al. | |

It is certified that error appears in the above-identified patent and that said Letters Patent is hereby corrected as shown below:

Column 20, Line 45, Claim 14, , "an angle a" should read -- an angle $a$ --

Signed and Sealed this

Thirteenth Day of May, 2008

JON W. DUDAS
*Director of the United States Patent and Trademark Office*